United States Patent [19]
Davis et al.

[11] Patent Number: 6,156,050
[45] Date of Patent: Dec. 5, 2000

[54] LANCET DEVICE

[75] Inventors: Richard M. Davis; Rowland W. Kanner, both of Guntersville, Ala.

[73] Assignee: Atrion Medical Products, Inc., Arab, Ala.

[21] Appl. No.: 09/379,648

[22] Filed: Aug. 24, 1999

Related U.S. Application Data

[63] Continuation of application No. 09/085,281, May 27, 1998, Pat. No. 5,984,940.
[60] Provisional application No. 60/047,857, May 29, 1997.

[51] Int. Cl.[7] .................................................. A61B 17/14
[52] U.S. Cl. .......................................... 606/181; 606/181
[58] Field of Search .................................. 606/181, 182, 606/184, 185

[56] References Cited

U.S. PATENT DOCUMENTS

| | | |
|---|---|---|
| 2,061 | 4/1841 | Osdel . |
| 3,797,488 | 3/1974 | Hurschman et al. . |
| 4,442,836 | 4/1984 | Meinecke et al. . |
| 4,469,110 | 9/1984 | Slama . |
| 4,535,769 | 8/1985 | Burns . |
| 4,577,630 | 3/1986 | Nitzsche et al. . |
| 4,628,929 | 12/1986 | Intengan et al. . |
| 4,895,147 | 1/1990 | Bodicky et al. . |
| 4,924,879 | 5/1990 | O'Brien . |
| 5,196,025 | 3/1993 | Ranalletta et al. ...................... 606/182 |
| 5,318,583 | 6/1994 | Rabenau et al. . |
| 5,318,584 | 6/1994 | Lange et al. . |
| 5,527,334 | 6/1996 | Kanner et al. ........................... 606/182 |
| 5,569,287 | 10/1996 | Tezuka et al. . |

FOREIGN PATENT DOCUMENTS

| | | |
|---|---|---|
| 0036443 | 9/1981 | European Pat. Off. . |
| 0458451 | 11/1991 | European Pat. Off. . |
| 6442010 | 3/1989 | Japan . |

*Primary Examiner*—Michael Buiz
*Assistant Examiner*—Vy Q. Bui
*Attorney, Agent, or Firm*—Trexler, Bushnell, Giangiorgi & Blackstone, Ltd.

[57] ABSTRACT

A lancet device for lancing skin with a lancing needle of a lancet. The lancet device includes a housing and a lancet holder within the housing which is engageable with the lancet and moveable along a longitudinal axis of the housing. The device also includes a cam which has an end surface engageable with the lancet holder, cocking structure, biasing means between the cocking structure and the cam, and a trigger which is engageable with the cam for preventing rotation of the cam during actuation of the cocking structure. Actuation of the cocking structure causes the biasing means to become loaded between the cam and cocking structure, wherein upon disengagement of the trigger from the cam, the cam rotates, causing the lancet holder to move generally along the longitudinal axis of the housing. The lancet holder includes a cam follower member which contacts the end surface of the cam. The cam follower member rides along the end surface of the cam when the cam rotates in the housing.

22 Claims, 17 Drawing Sheets

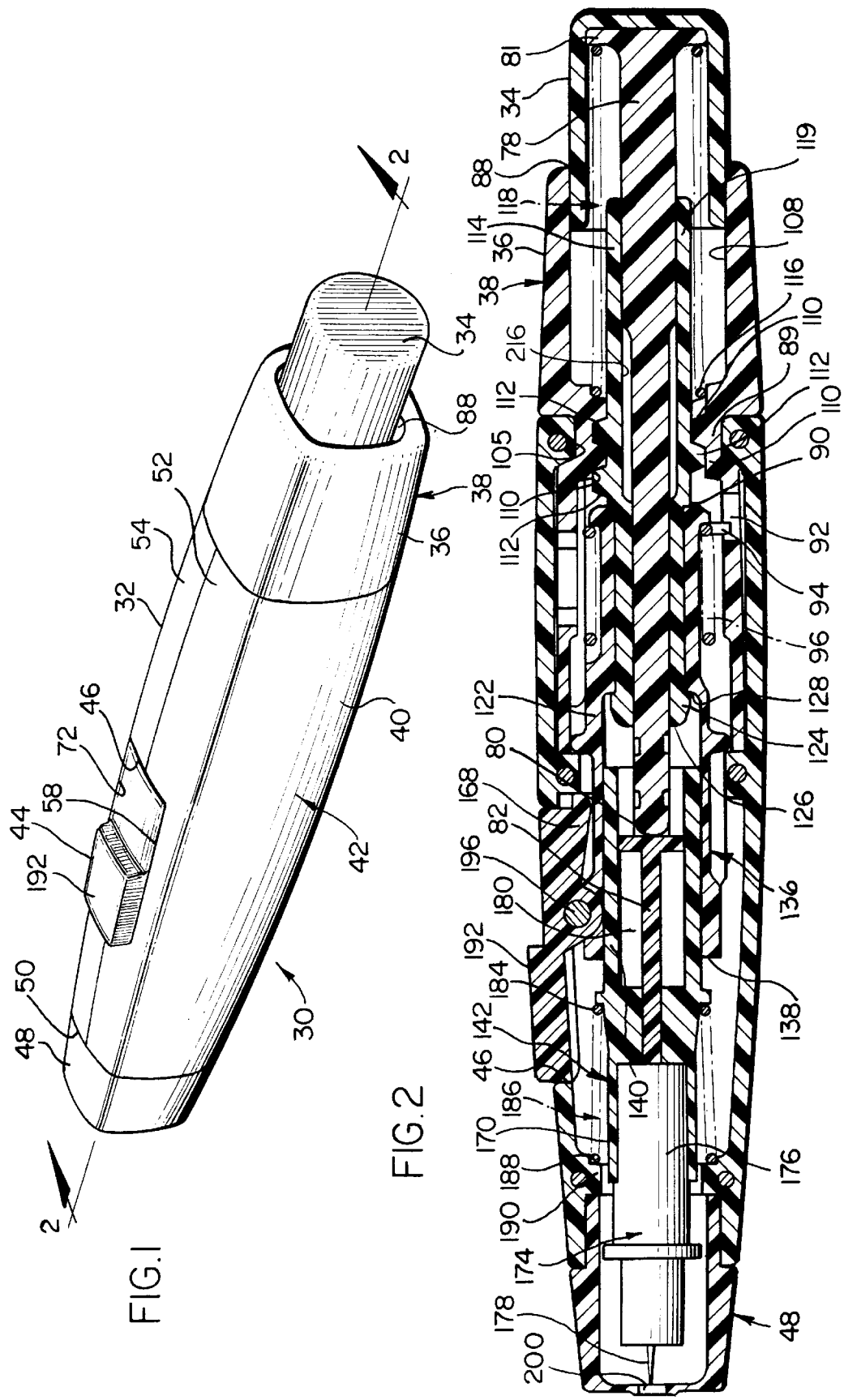

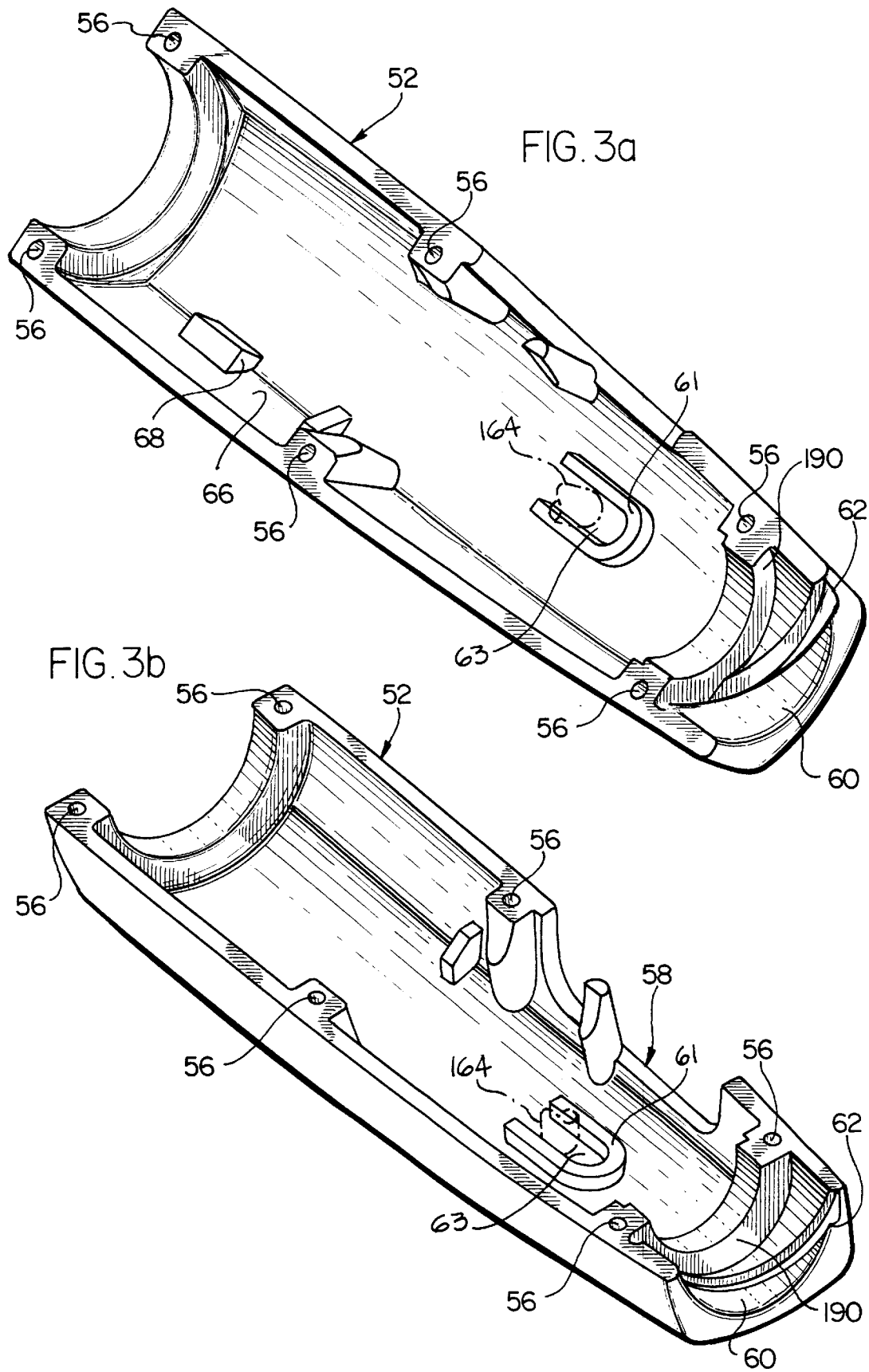

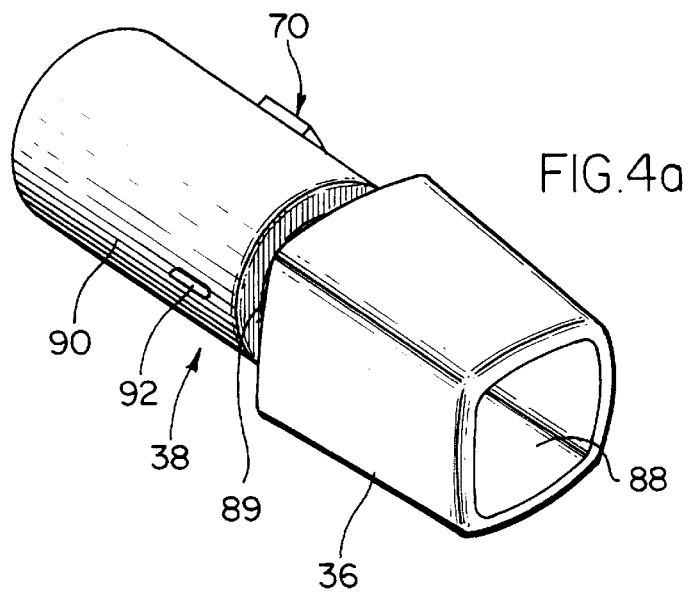
FIG.4a
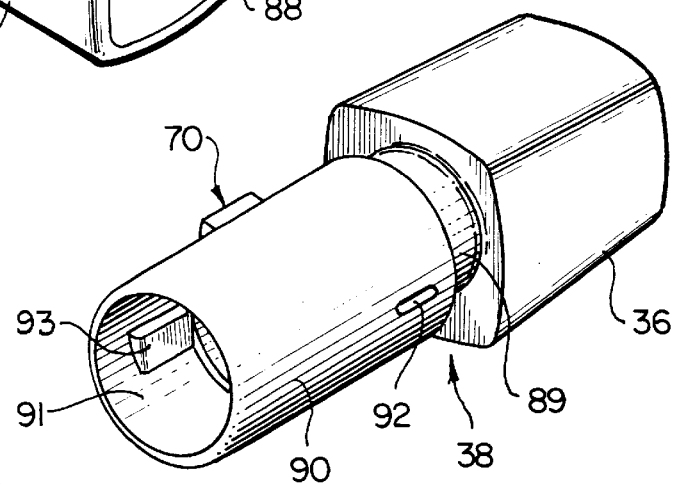
FIG.4b
FIG.4c
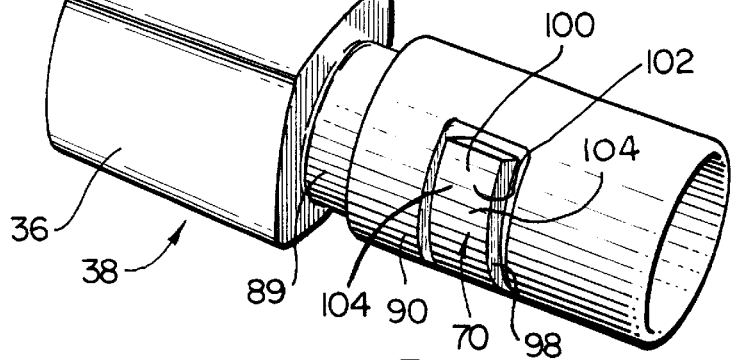
FIG.5
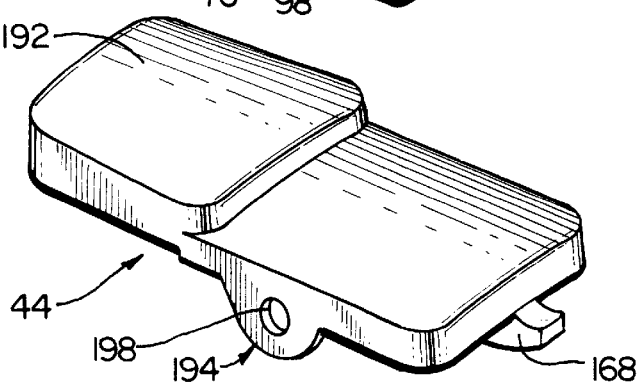

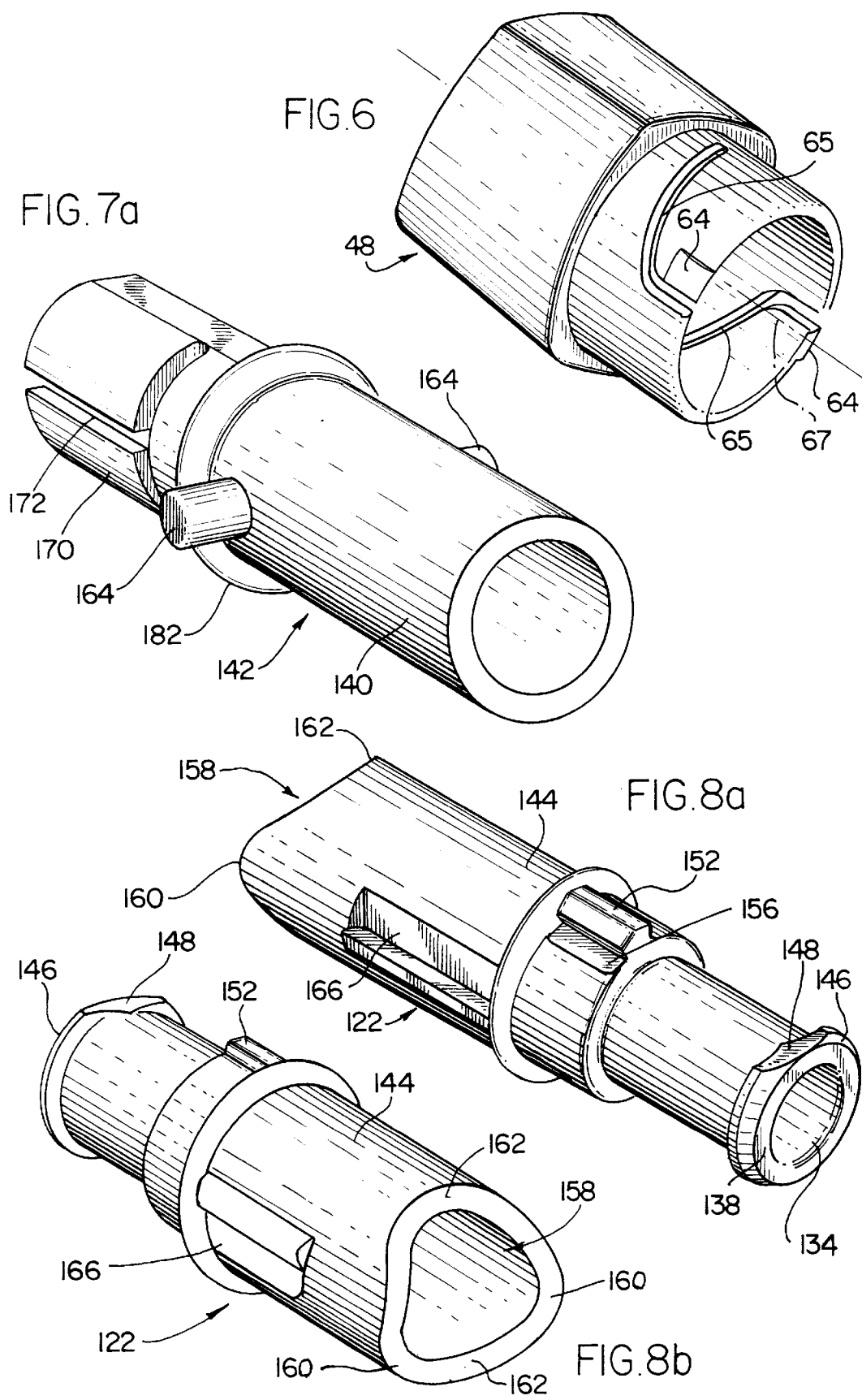

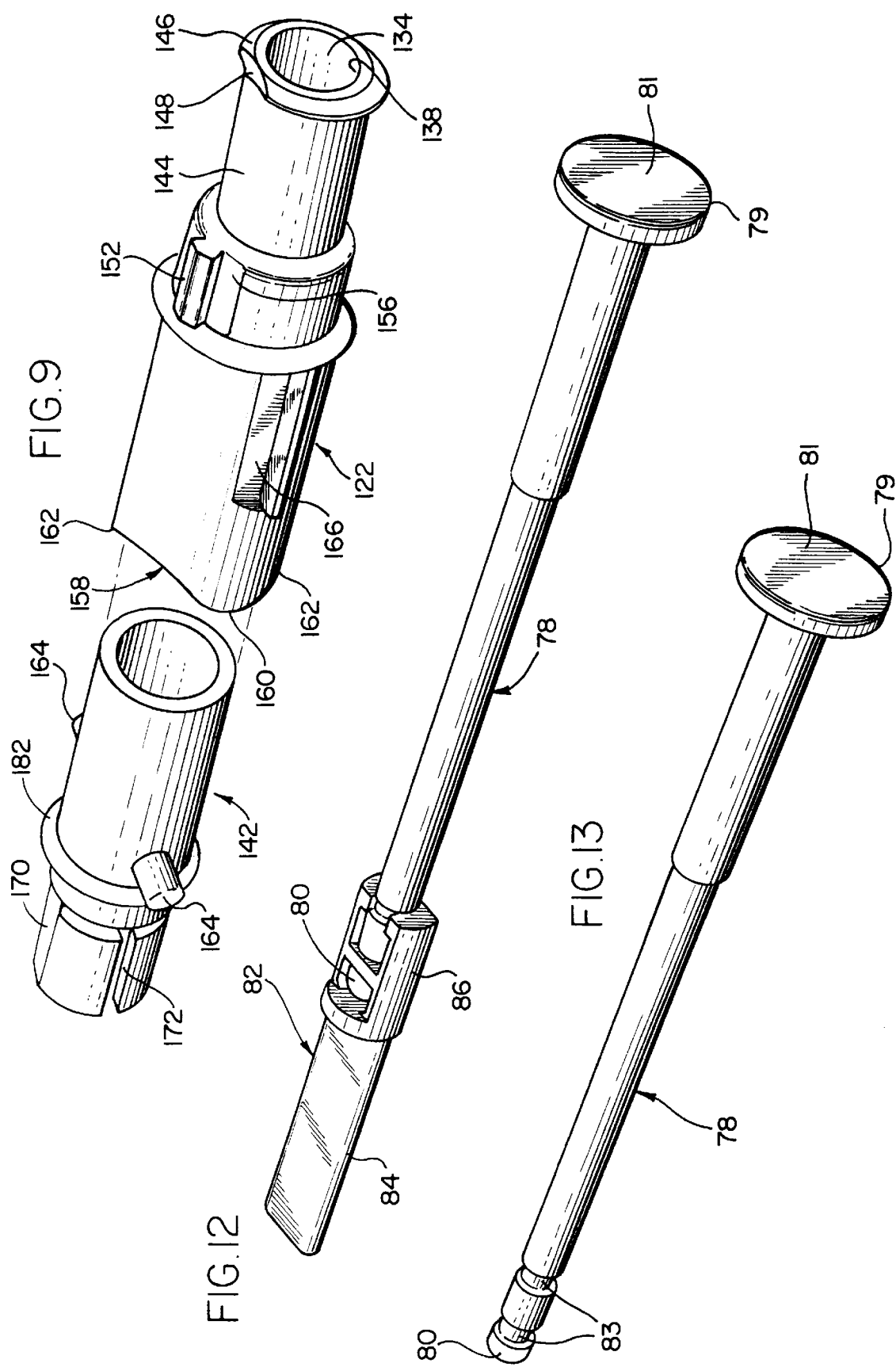

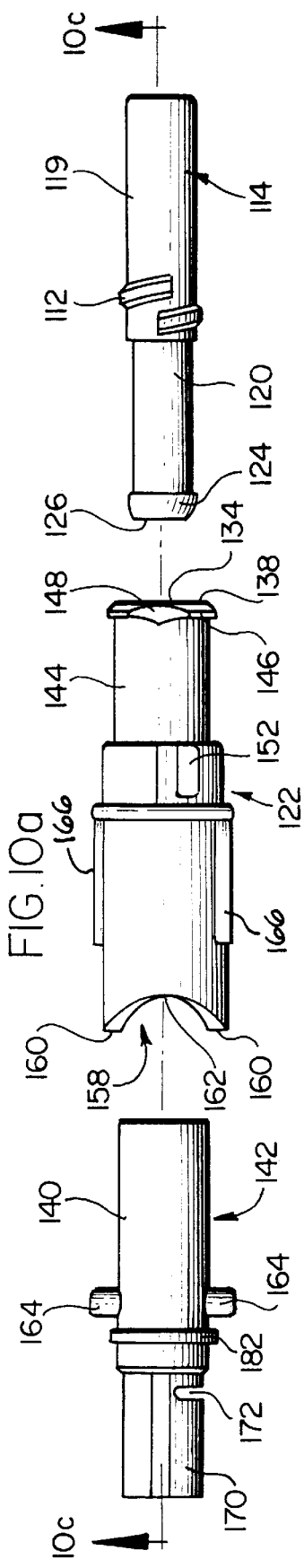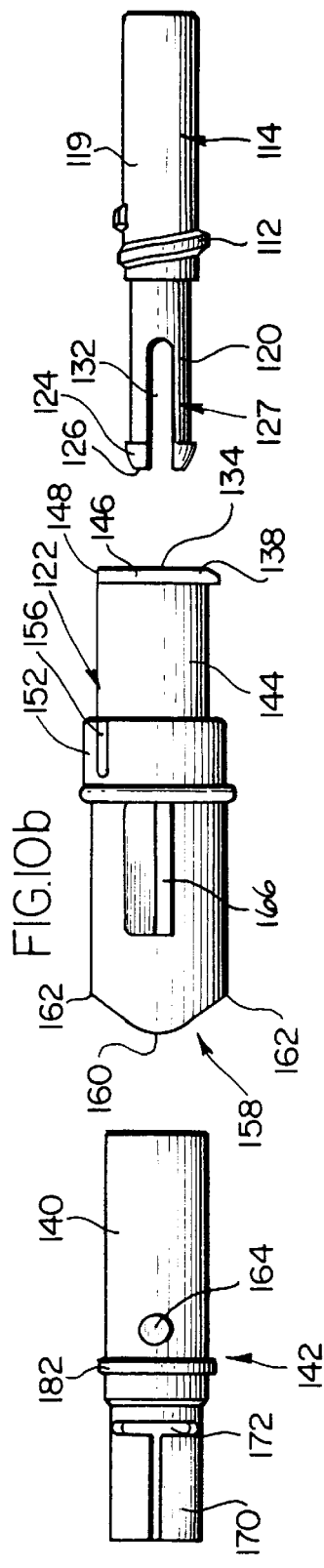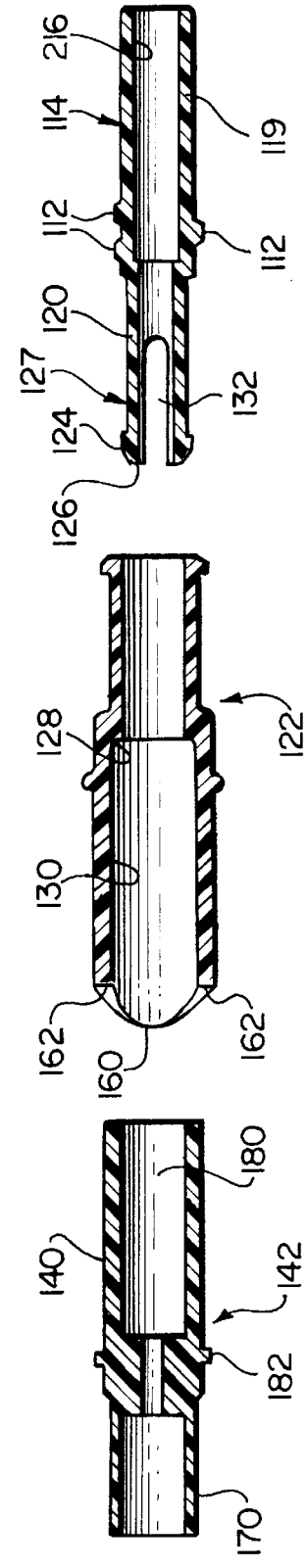

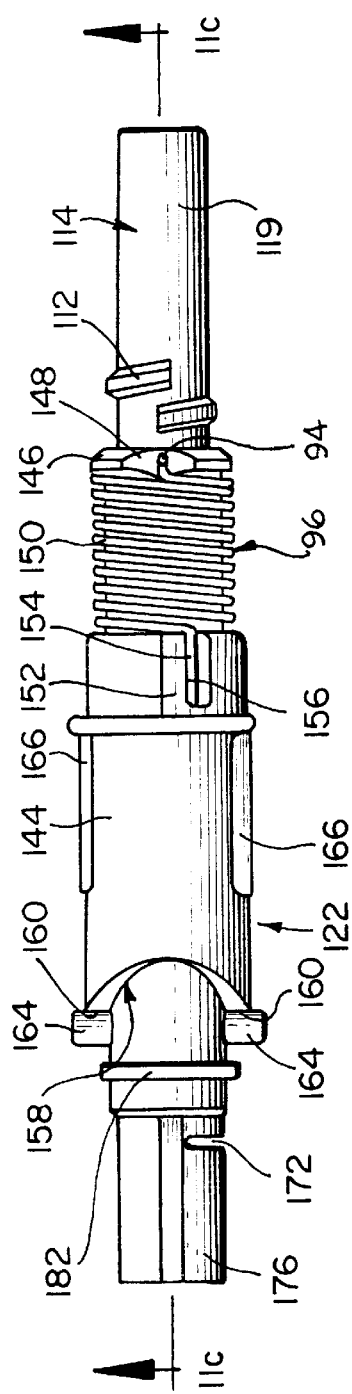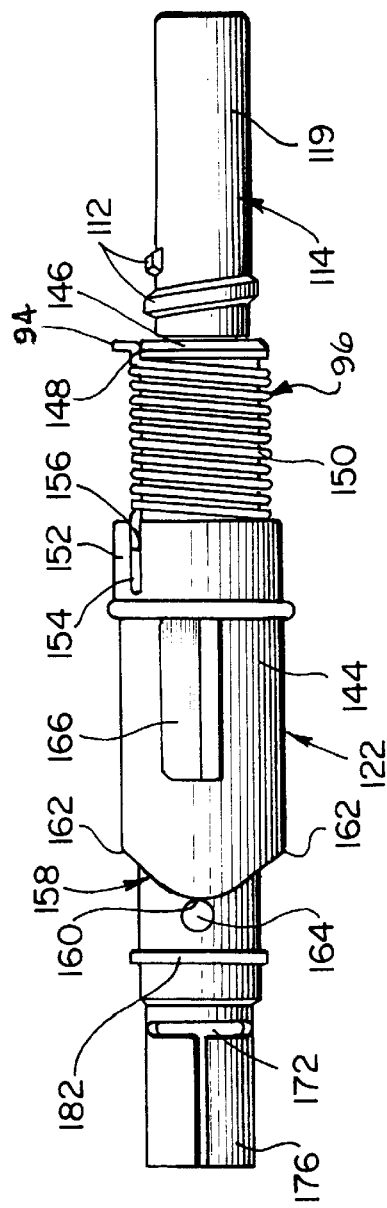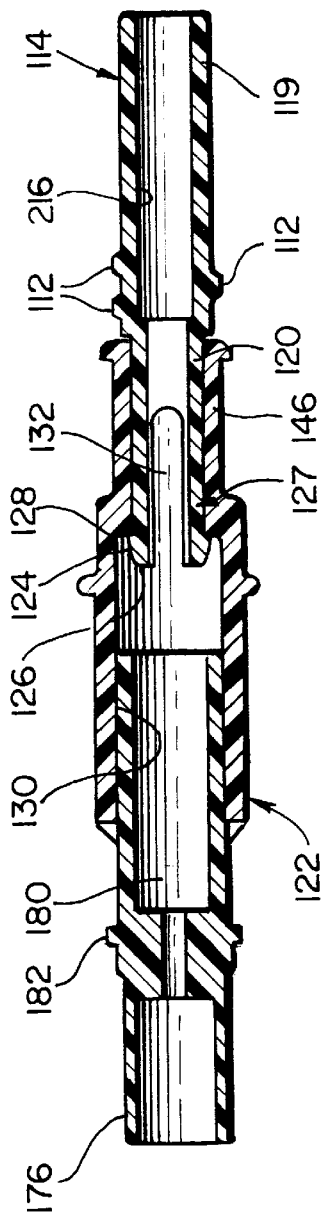

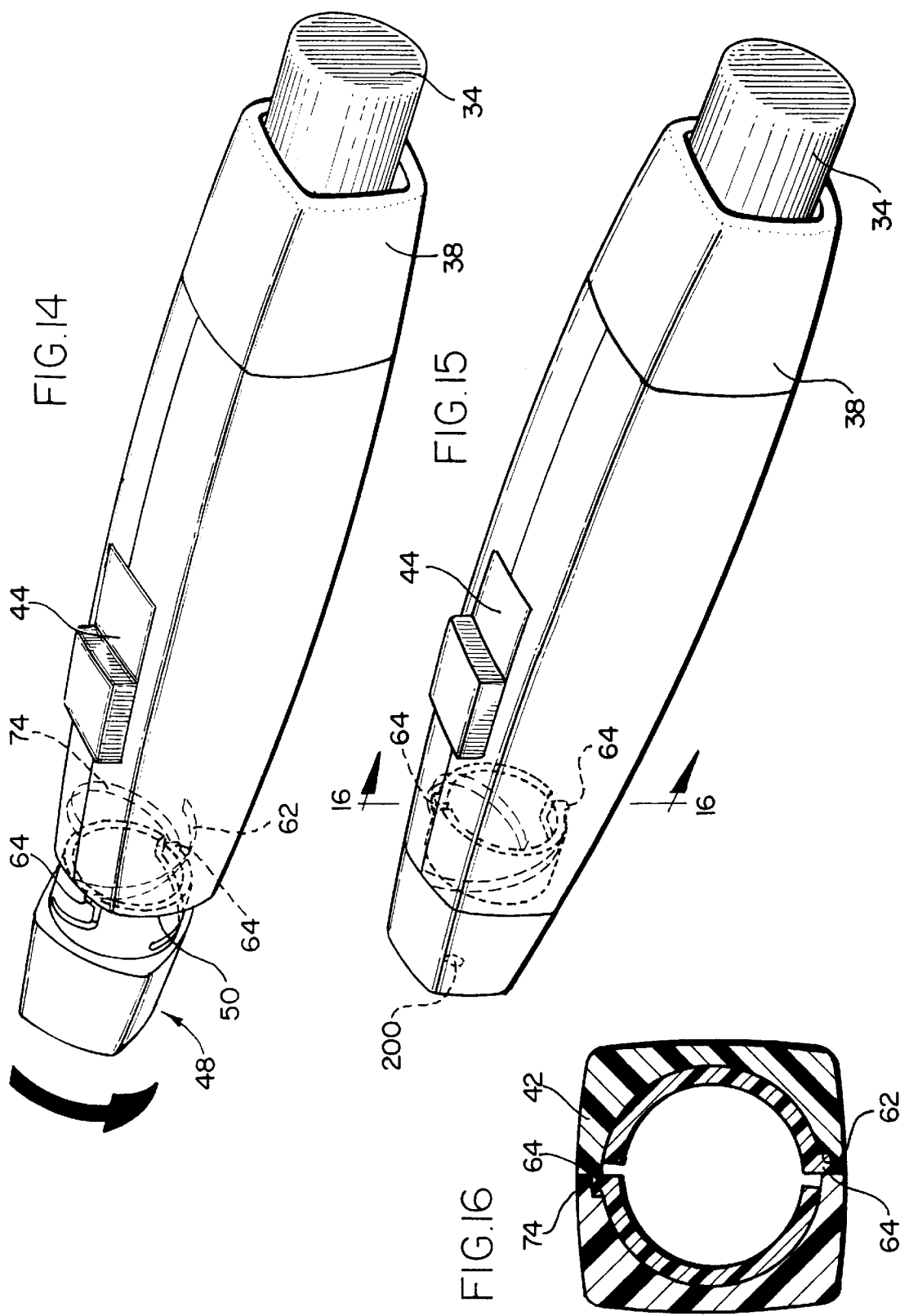

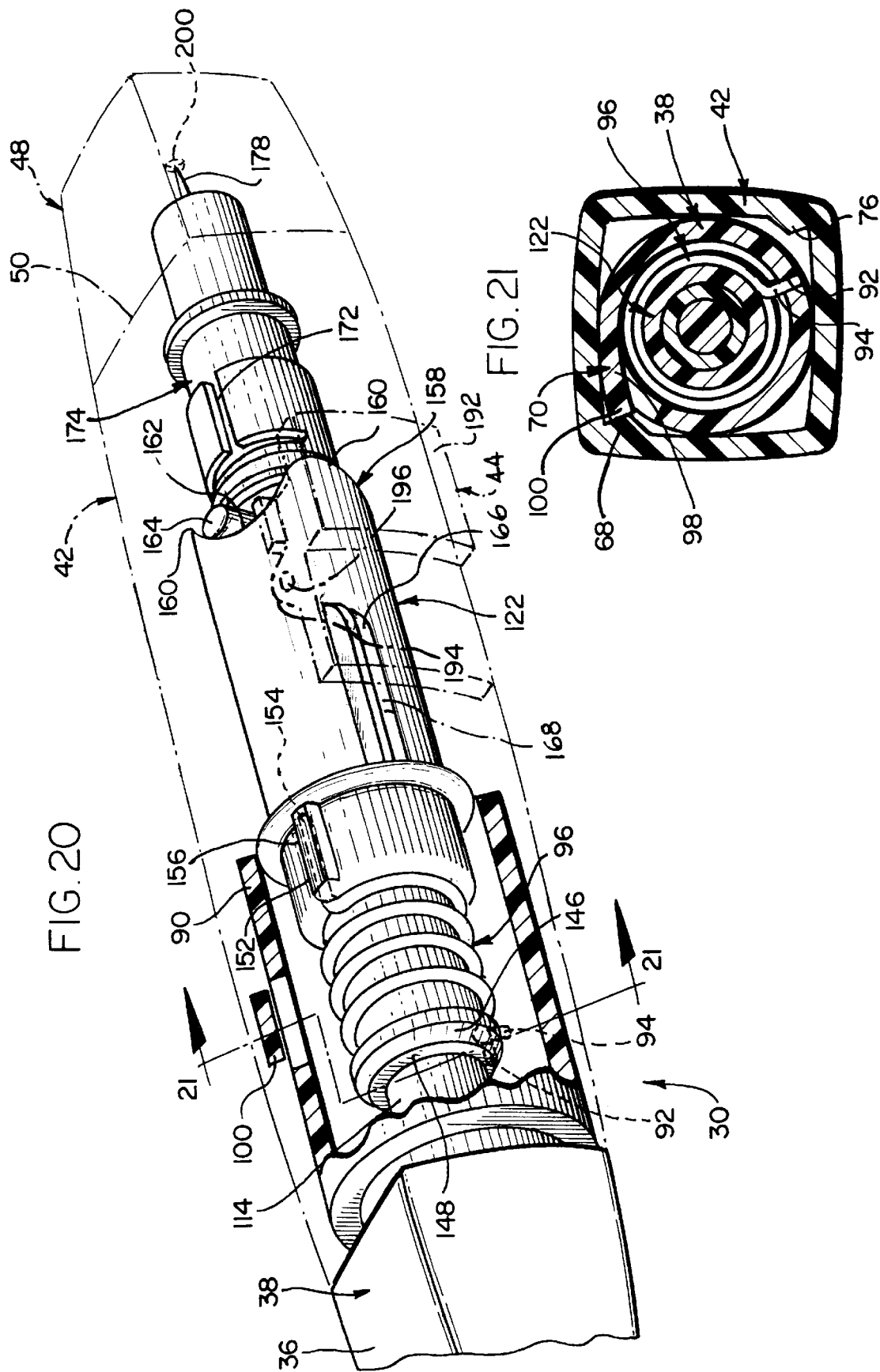

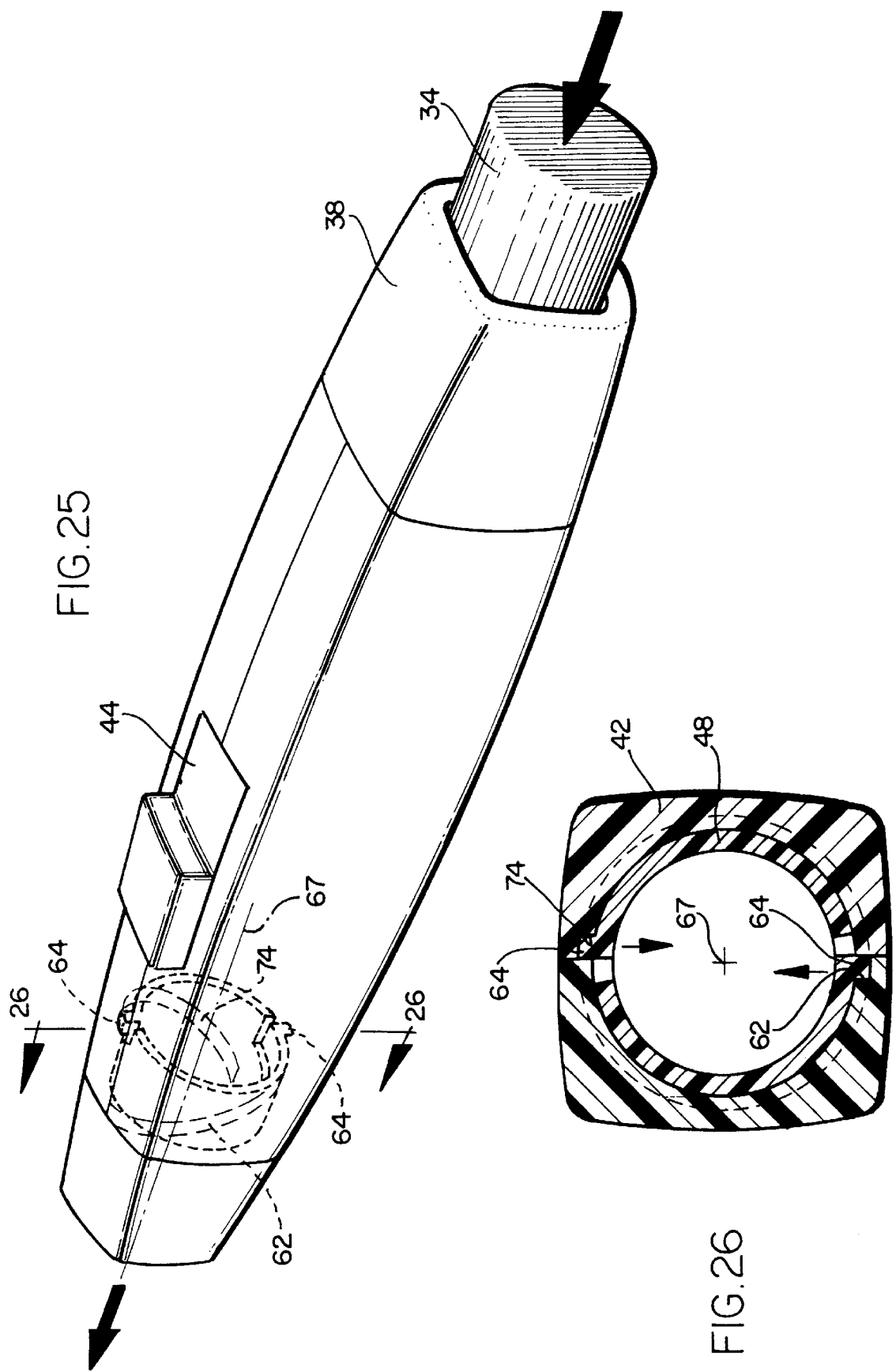

LANCET DEVICE

RELATED APPLICATIONS

This application is a continuation of U.S. patent application Ser. No. 09/085,281, filed on May 27, 1998 patented as U.S. Pat. No. 5,984,940, which claims the benefit of U.S. Provisional Application No. 60/047,857, filed May 29, 1997.

BACKGROUND OF THE INVENTION

The present invention relates generally to a lancet device for lancing a human fingertip to obtain a small amount of blood for diagnostic purposes, and relates more specifically to a novel lancet device which is held like a writing instrument while being used to lance a fingertip.

In many situations, it is desirable to obtain a small amount of human blood for diagnostic purposes. For example, a person who is diabetic may want to obtain a small amount of his or her blood in order to test the blood-sugar level thereof and determine whether an insulin shot should be administered.

Presently, lancet devices are available for a person to use to lance a fingertip. Typically, these devices have a "firing" end from which a lancing needle extends through a hole when the device is "fired." While these devices are generally effective, the devices which are presently available present many disadvantages. For example, many of the devices are bulky and difficult to hold. Moreover, many of the devices have a "trigger", or actuator button, relatively far from the firing end. As a result, it is difficult for a user to maintain the firing end of the device against the fingertip while firing the device. Additionally, many of the presently available devices provide that the lancing needle extends from the firing end as the device is being "cocked", or prepared for firing, and fail to provide that the lancing needle can be quickly and easily removed and disposed of after the device is fired. Consequently, one may get accidentally stuck by the lancing needle while removing the lancing needle from the device. While this accidental sticking may not be especially detrimental in a situation such as when a person who is diabetic is personally using the lancet device at home to lance him or herself, this accidental sticking by the lancing needle may be extremely undesirable in some situations such as when a nurse is using the lancet device on a patient who has AIDS.

While some of the devices presently available provide that the lancing needle can be ejected without having to touch the lancing needle, these devices require that one remove a tip platform before ejecting the lancing needle. However, the tip platform may also have blood thereon because the tip platform is placed against the fingertip immediately before the device is fired, and when the device is fired, the lancing needle extends through and retracts back into a hole in the tip platform. Because the tip platform may have blood thereon, it is desirable to avoid having to touch the tip platform in order to eject the lancing needle.

Other disadvantages presented by the lancet devices that are presently available include requiring a great amount of force from the user in order to cock the device, fire the device, or eject the lancing needle from the device.

For the foregoing reasons, there is a need for a novel lancet device structured in accordance with the present invention. The present invention is directed to eliminated the problems discussed hereinabove.

OBJECTS AND SUMMARY

A general object of the present invention is to provide a novel lancet device which is both easy to hold and use.

Another object of the present invention is to provide a novel lancet device that has a trigger relatively close to its firing end.

Still another object of the present invention is to provide a novel lancet device which does not extend a lancing needle when the device is cocked.

Still yet another object of the present invention is to provide a novel lancet device which allows a lancing needle to be quickly and easily removed and disposed of after the device is fired without having to touch a tip platform before doing so.

Still a further object of the present invention is to provide a novel lancet device which does not require a significant amount of force to cock or fire, and which does not require a significant amount of force to eject a lancing needle therefrom.

Briefly, and in accordance with the foregoing, the present invention envisions a lancet device for lancing skin with a lancing needle of a lancet. The lancet device includes a housing and a lancet holder within the housing which is engageable with the lancet. The device also includes a cam which has an end surface in contact with the lancet holder, cocking structure, biasing means between the cocking structure and the cam, and a trigger which is engageable with the cam for preventing rotation of the cam during actuation of the cocking structure and preventing movement of the lancet holder. Actuation of the cocking structure causes the biasing means to become loaded between the cam and cocking structure, wherein the cam rotates upon disengagement of the trigger from the cam, causing the lancet holder to move generally along the longitudinal axis of the housing. The lancet holder includes at least cam follower member which contacts the end surface of the cam. The cam follower member rides along the end surface of the cam when the cam rotates in the housing.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which:

FIG. 1 is a perspective view of a novel lancet device structured in accordance with the present invention;

FIG. 2 is a cross-sectional view of the lancet device shown in FIG. 1 taken along line 2—2 of FIG. 1;

FIG. 3*a* is a perspective view of a first half of a housing of the lancet device of FIGS. 1 and 2 showing a stop on the housing;

FIG. 3*b* is another perspective view of the first half of the housing of the lancet device of FIGS. 1 and 2 showing a wall forming half of an aperture in the housing for receiving a trigger;

FIGS. 4*a*, 4*b* and 4*c* are perspective views of a cocking knob of the lancet device of FIGS. 1 and 2;

FIG. 5 is a perspective view of a trigger of the lancet device of FIGS. 1 and 2;

FIG. 6 is a perspective view of a platform tip of the lancet device of FIGS. 1 and 2;

FIG. 7*a* is a perspective view of a lancet holder of the lancet device of FIGS. 1 and 2;

FIG. 7d is a cross-sectional view of the lancet holder of FIG. 7a–7c, taken along line 7d—7d of FIG. 7a;

FIG. 8a and 8b are perspective views of a cam of the lancet device of FIGS. 1 and 2;

FIG. 9 is an exploded, perspective view of the cam and lancet holder of the lancet device of FIGS. 1 and 2;

FIG. 10a is a side, elevational, exploded view of the depth adjustment screw, the cam, and the lancet holder of the lancet device of FIGS. 1 and 2;

FIG. 10b is a top plan, exploded view of the depth adjustment screw, the cam, and the lancet holder of the lancet device of FIGS. 1 and 2;

FIG. 10c is a cross-sectional, exploded view, taken along line 10c—10c of FIG. 10a, of the depth adjustment screw, the cam, and the lancet holder of the lancet device of FIGS. 1 and 2;

FIG. 11a is a side, elevational view showing engagement of the depth adjustment screw, the cam, and the lancet holder of the lancet device of FIGS. 1 and 2;

FIG. 11b is a top plan view showing engagement of the depth adjustment screw, the cam, and the lancet holder of the lancet device of FIGS. 1 and 2;

FIG. 11c is a cross-sectional view, taken along line 11c—11c of FIG. 11a, showing engagement of the depth adjustment screw, the cam, and the lancet holder of the lancet device of FIGS. 1 and 2;

FIG. 12 is a perspective view of an ejector rod and ejector blade of the lancet device of FIGS. 1 and 2;

FIG. 13 is a perspective view of the ejector rod of FIG. 12, showing the ejector blade disengaged therefrom;

FIG. 14 is a schematic view of the lancet device of FIGS. 1 and 2 showing the tip platform being screwed into the housing of the lancet device;

FIG. 15 is a schematic view of the lancet device of FIGS. 1 and 2 showing the tip platform having been screwed into the housing of the lancet device;

FIG. 16 is a cross-sectional view of the lancet device of FIG. 15, taken along line 16—16 of FIG. 15, showing flanges on the tip platform engaged with helical grooves on the housing of the lancet device;

FIG. 20 is a schematic of certain components of the lancet device of FIGS. 1 and 2, showing engagement of the detent flange on the cocking knob with the stop on the housing after the cocking knob has been rotated one hundred eighty degrees to cock the lancet device;

FIG. 21 is a cross-sectional view of the lancet device of FIG. 20, taken along line 21—21 of FIG. 20, showing the detent flange on the cocking knob secured against the stop on the housing;

FIG. 25 is a schematic view of the lancet device of FIG. 24 showing the tip platform being ejected along with the lancet from the lancet device as a result of the thumb button being pushed; and FIG. 26 is a cross-sectional view of the lancet device of FIG. 25, taken along line 26—26 of FIG. 25, showing flanges on the tip platform moving inward towards a central axis of the tip platform clearing helical grooves on the housing of the lancet device.

DETAILED DESCRIPTION OF THE PREFERRED EMBODIMENT

Figure 7B:
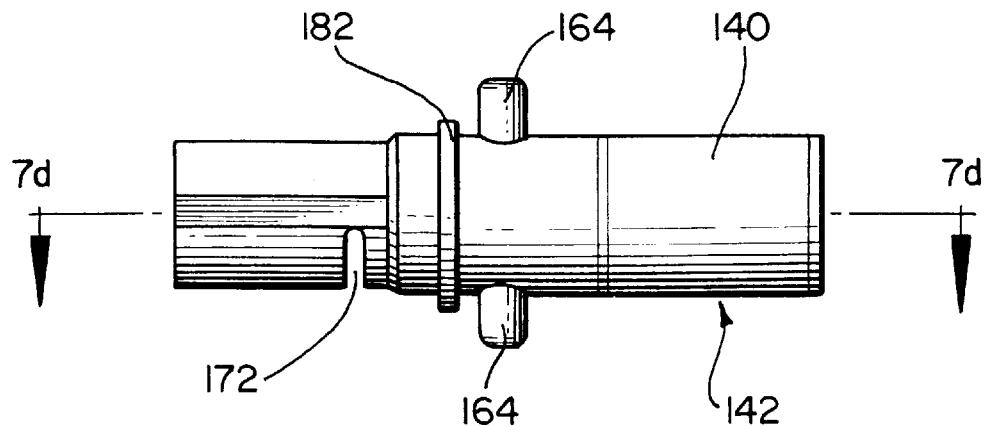
FIG. 7*b* is a top, elevational view of the lancet holder of FIG. 7*a*.
Figure 7C:
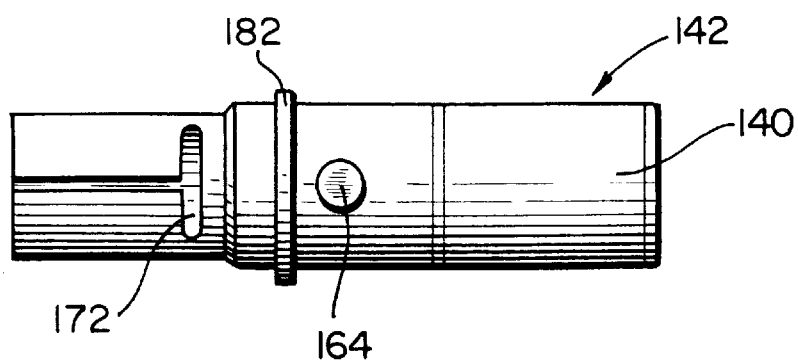
FIG. 7c is a side plan view of the lancet holder of FIGS. 7a and 7b.
Figure 7D:
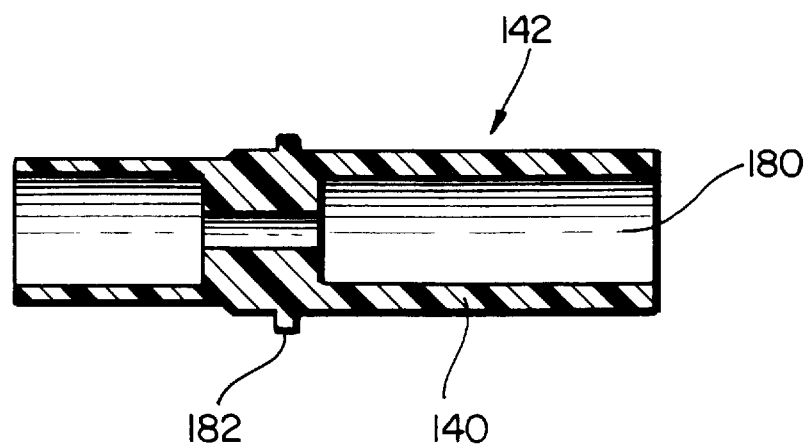
Figure 8C:
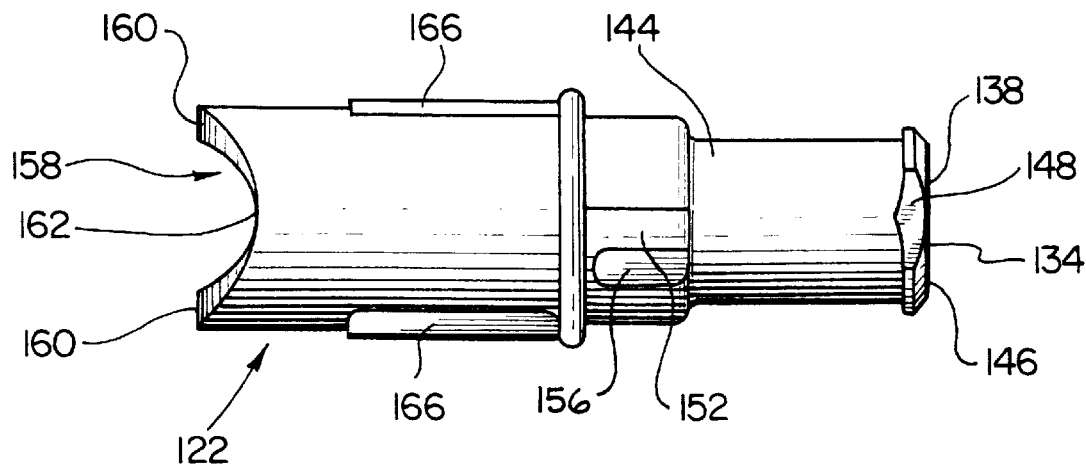
FIG. 8c is a top, elevational view of the cam of FIGS. 8a and 8b.
Figure 8D:
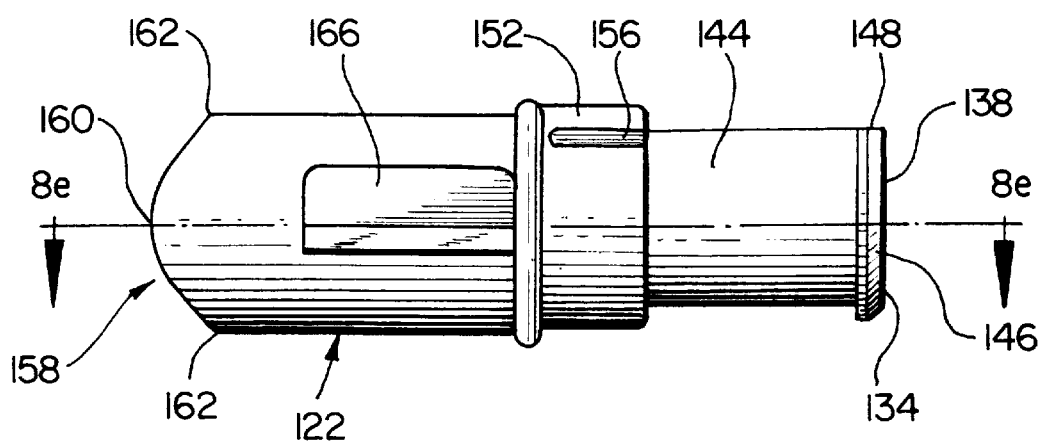
FIG. 8d is a side plan view of the cam of FIGS. 8a, 8b and 8c.
Figure 8E:
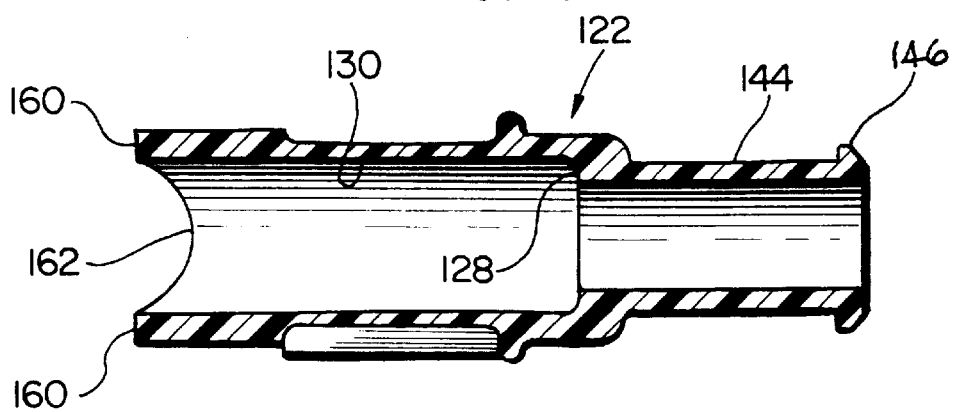
FIG. 8e is a cross-sectional view of the cam of FIGS. 8a–8d, taken along line 8e–8e of FIG. 8d.

While the present invention may be susceptible to embodiment in different forms, there is shown in the drawings, and herein will be described in detail, an embodiment with the understanding that the present description is to be considered an exemplification of the principles of the invention and is not intended to limit the invention to that as illustrated and described herein.

Shown in the drawings is a novel lancet device 30 designed to be used to pierce a human fingertip in order to obtain blood for diagnostic purposes. For example, the lancet device 30 can be used to pierce the fingertip of a person who is diabetic so that the person can obtain blood, and then test the sugar level thereof.

As shown in FIG. 1, an external surface 32 of the lancet device 30 is formed by a thumb button 34, a top portion 36 of a cocking knob 38, an external surface 40 of a housing 42, a trigger 44 which is set in an aperture 46 in the housing 42 relatively close to a tip platform 48 which is screwed into at an end 50 of the housing 42.

As shown in FIG. 1, when the tip platform 48 is screwed into the end 50 of the housing 42, the tip platform 48 forms one end of the lancet device 30. When the tip platform 48 is not screwed into the end 50 of the housing 42, the end 50 of the housing 42 forms this end of the lancet device 30.

The housing 42 of the lancet device 30 is formed of a first half 52 and a second half 54. When the first half 52 of the housing 42 is connected to the second half 54 of the housing 42, the two halves 52 and 54 form the housing 42 as shown in FIGS. 1 and 2. The two halves 52 and 54 of the housing 42 are connectable to each other by way of screws or other connecting means, such as by being snapped together. Shown alone in FIGS. 3a and 3b is the first half 52 of the housing 42. As shown, the first half 52 of the housing 42 may have holes 56 for receiving screws (not shown) which connect the first half 52 of the housing 42 to the second half 54 of the housing 42. The screws extend through the holes 56 in the first half 52 of the housing 42, and thread into threaded holes (not shown) in the second half 54 of the housing 42 in order to connect the first half 52 of the housing 42 to the second half 54 of the housing 42. As shown in FIG. 3*b*, a wall 58 of the first half 52 of the housing 42 forms half of the aperture 46, shown in FIGS. 1 and 2, in which the trigger 44 is set when the two halves 52 and 54 of the housing 42 are interconnected. As shown in FIGS. 3*a* and 3*b*, at the end 60 of the first half 52 of the housing 42 is a helical groove 62. As shown in FIGS. 14–16, the helical groove 62 receives one of two flanges 64 on the tip platform 48 when the tip platform 48 is screwed into the end 50 of the housing 42. As shown in FIGS. 3*a* and 3*b*, a U-shaped wall 61 on the interior surface 66 of the first half of the housing 42 provides a groove 63 for receiving one of two cam follower members 164 which will be explained more fully later herein. FIG. 2 shows the tip platform 48 screwed into the housing 42.

The tip platform 48 is shown alone in FIG. 6. As shown, each of the flanges 64 on the tip platform 48 are located adjacent a helical slot 65. The helical slots 65 provide that the flanges 64 can be urged toward a central axis 67 of the platform tip 48. The flanges 64 will be urged toward the central axis 67 to allow the flanges 64 to clear the helical grooves 62 near the end 50 of the housing 42 and allow the tip platform 48 to be ejected from the lancet device 30 along with a lancing needle. The simultaneous ejection of the tip platform 48 and lancing needle will be explained in more detail later hereinbelow.

Figures 18, 19:
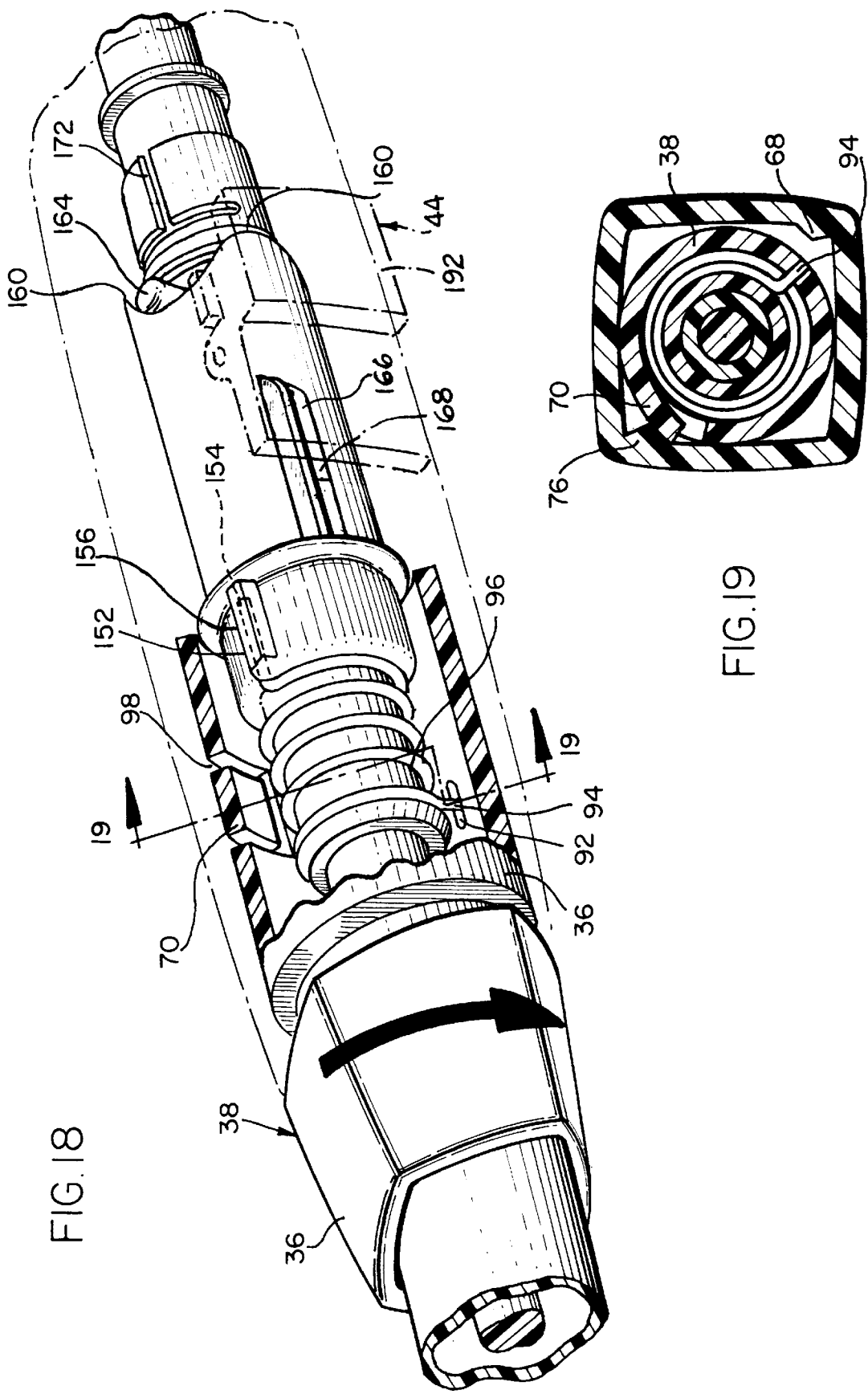
FIG. 18 is a schematic of certain components of the lancet device of FIGS. 1 and 2, showing rotation of a cocking knob to cock the lancet device.
FIG. 19 is a cross-sectional view of the lancet device of FIG. 18, taken along line 19—19 of FIG. 18, showing a detent flange on the cocking knob moving towards a stop on the housing as the cocking knob is being rotated.

As shown in FIG. 3*a*, on the internal surface 66 of the first half 52 of the housing 42 is a stop 68, comprising a flange, which engages a one way detent finger 70 on the cocking knob 38, as shown in FIGS. 18, 19 and 21, when the cocking knob 38 is rotated to cock the lancet device 30 and prepare the lancet device 30 for firing. The engagement of the stop 68 on the housing 42 with the one-way detent finger 70 on the cocking knob 38 will be more fully explained later hereinbelow when cocking of the lancet device 30 is explained in detail.

The second half 54 of the housing 42 is structured very much like the first half 52 of the housing 42. For example, the second half 54 of the housing 42 has a wall 72 much like wall 58 of the first half of the housing 42 such that when the first half 52 of the housing 42 is connected to the second half of the housing 42, the aperture 46 in the housing 42 is formed for receiving the trigger 44. Also, the end of the second half 54 of the housing 42, like the first half 52 of the housing 42, has a helical groove 74 for receiving one of two flanges 64 on the tip platform 48. The second half 54 of the housing also has a stop 76 identical to the stop 68 on the first half of the housing 42. Additionally, the second half 54 of the housing 42 includes a U-shaped wall 61 on its interior surface which provides a groove 63 for receiving the other cam follower member 164 of the lancet holder 142. As shown in FIG. 21, when the two halves 52 and 54 of the housing 42 are interconnected to form the housing 42, the stops 68 and 76 oppose each other such that they are located about 180 degrees away from each other within the internal surface of the housing 42.

As shown in FIG. 2, the thumb button 34 forms one end of the lancet device 30 and is essentially a cap connected to an ejector rod 78 which extends through and along a central axis of the lancet device 30. At one end 79 of the ejector rod 78 is a platform 81 to which the thumb button 34 is secured. The thumb button 34 may be adhesively secured to the ejector rod platform 81. An ejector blade 82 is secured to the other end 80 of the ejector rod 78. The shape of both the ejector rod 78 and the ejector blade 82 is best depicted in FIG. 12. The ejector blade 82 has a blade portion 84 which is flat and wide, and has an ejector rod engaging portion 86 that is shaped and designed for snapping, securable engagement with the end 80 of the ejector rod 78. As shown in FIG. 13, the ejector rod 78 has indents 83 for engaging the ejector rod engaging portion 86 of the ejector blade 82. When the ejector rod 78 is snapped into engagement with the ejector blade 82, the ejector rod 78 can rotate in relation to the ejector blade 82.

As shown in FIGS. 1 and 2, the thumb button 34 extends into an opening 88 in the top portion 36 of the cocking knob 38. The structure of the cocking knob 38 will now be described with reference to FIGS. 4*a*, 4*b* and 4*c*. The cocking knob 38 has a top portion 36, a middle portion 89, and a bottom portion 90. The cocking knob 38 has a central throughbore 91 which defines the opening 88 in the top portion 36 of the cocking knob 38 into which the thumb button 34 extends. The thumb button 34 can be pushed into the opening 88 in the top portion 36 of the cocking knob 38 in order to eject a lancing needle and a tip platform 48 from the lancet device 30. The thumb button 34 can also be rotated in relation to the cocking knob 38 in order to set the distance a lancing needle will extend from a tip platform 48 of the lancet device 30 when the lancet device 30 is fired. However, these features of the lancet device 30 will be described more fully later hereinbelow.

Figure 17:
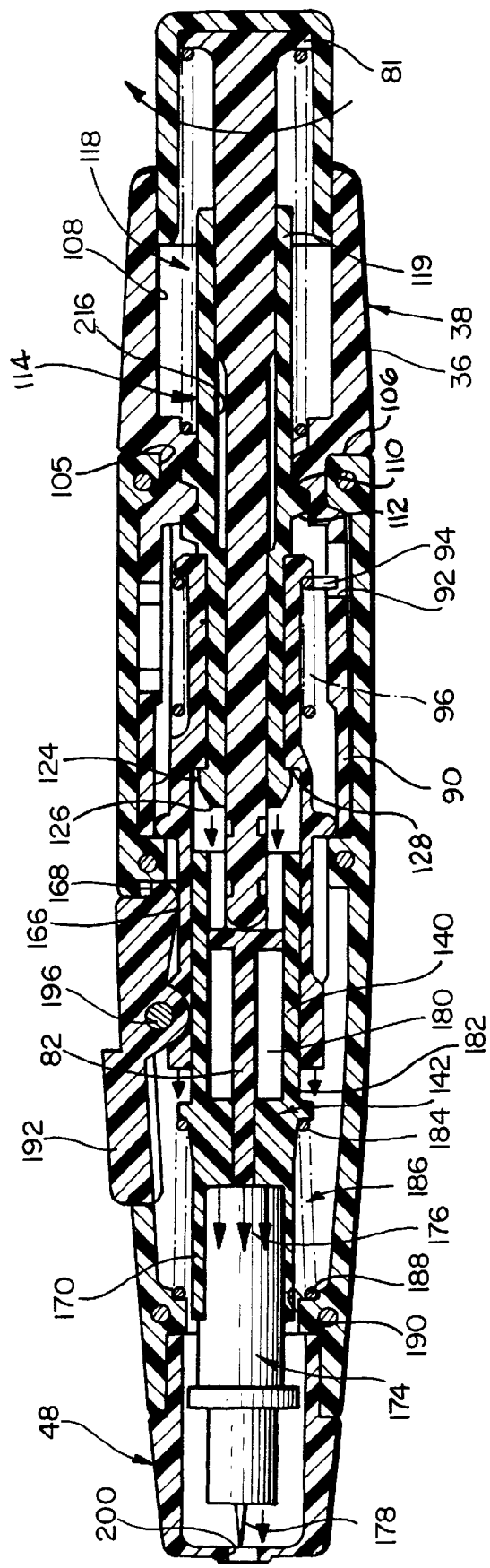
FIG. 17 is a cross-sectional view of the lancet device shown in FIG. 1, taken along line 2—2 of FIG. 1, showing a thumb button being rotated in order to set the depth at which a lancing needle will extend when the lancet device is fired.
Figure 22:
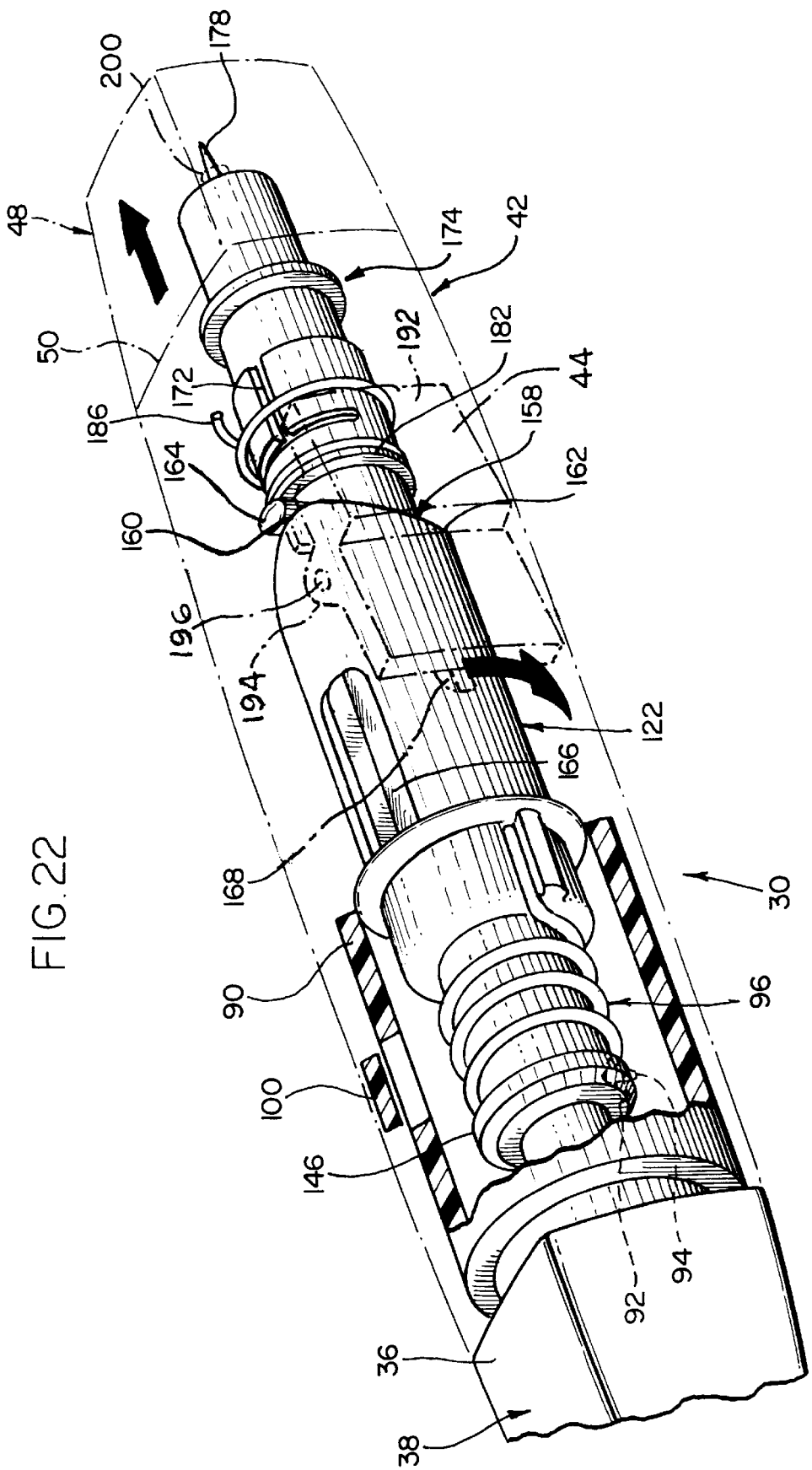
FIG. 22 is a schematic of certain components of the lancet device of FIGS. 1 and 2, showing the lancet device during firing, after a trigger has been pressed, and showing extension of a lancing needle from a hole in the tip platform.
Figure 23:
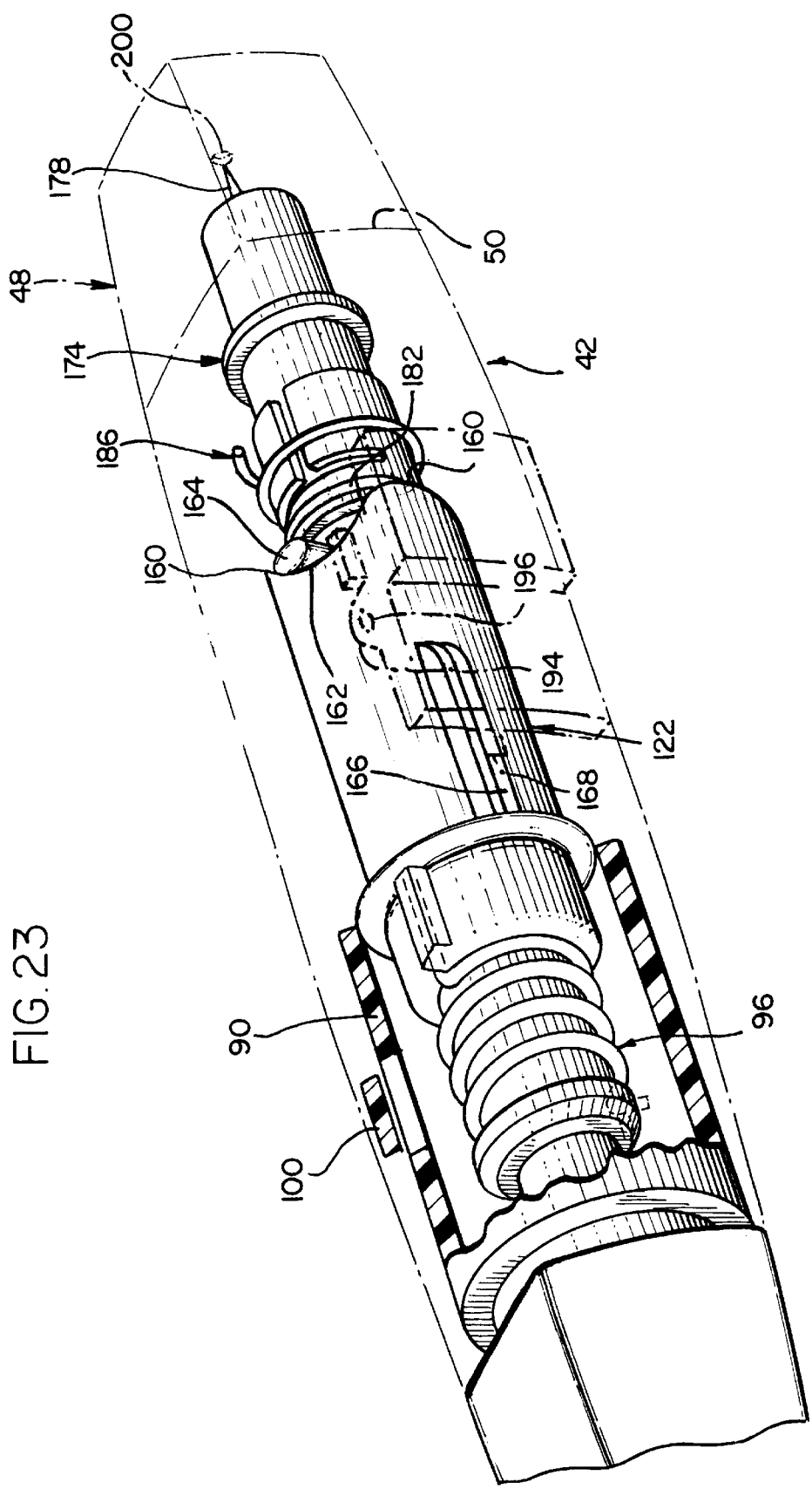
FIG. 23 is a schematic of certain components of the lancet device of FIGS. 1 and 2, showing the lancet device after firing, showing a sear member on the trigger re-engaged against a trigger stop on the cam, and showing the lancing needle having retracted back into the hole in the tip platform.
Figure 24:
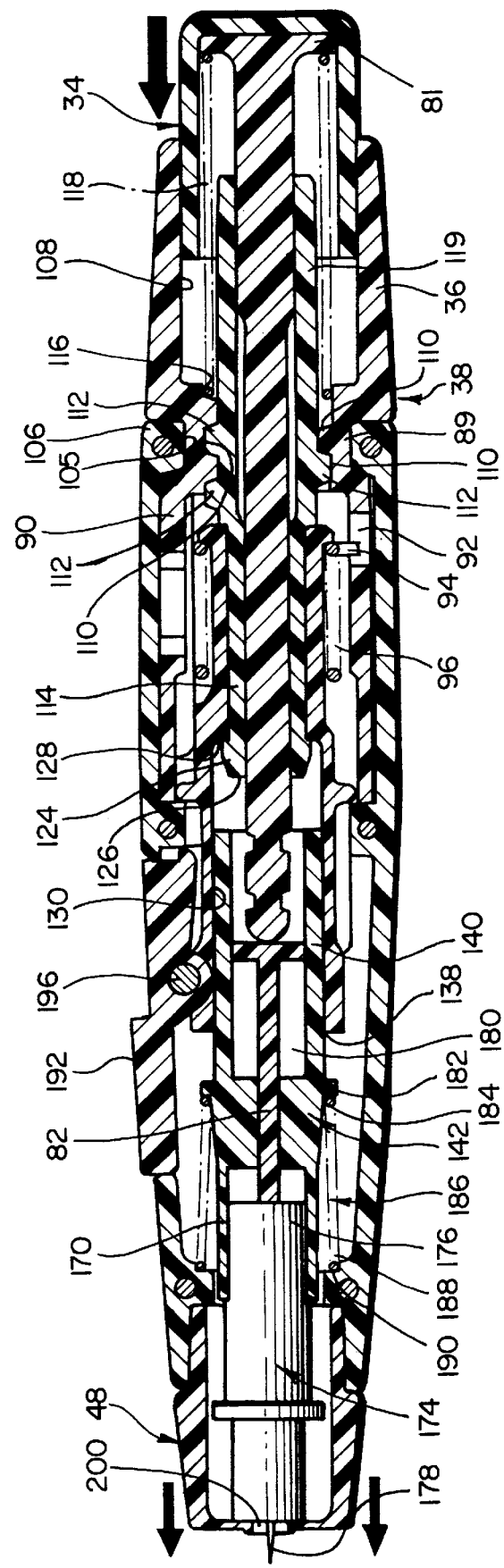
FIG. 24 is a cross-sectional view of the lancet device shown in FIG. 1, taken along line 2—2 of FIG. 1, showing a thumb button being pushed in order to simultaneously eject the tip platform and the lancet from the lancet device.

The bottom portion 90 of the cocking knob 38 has a slot 92 therein for receiving a top portion 94 of a drive spring 96 as shown in FIGS. 2, 18, 20, 21, 22, 23 and 24. Preferably, the drive spring 96 is a torsion spring. As shown in FIGS. 4*a*, 4*b*, 4*c*, 18, 20, 21, 22 and 23, also formed in the bottom portion 90 of the cocking knob 38 is the one way detent finger 70. The one way detent finger 70 is comprised of a flexible finger 98 having a detent flange 100 formed thereon. An angled wall 102 forms a side 104 of the detent flange 100. As shown in FIGS. 2, 17 and 24, the bottom portion 90 and the middle portion 89 of the cocking knob 38 are disposed in the housing 42, and the middle portion 89 of the cocking knob 38 engages an inwardly extending shoulder 105 at an end 106 of the housing 42 thus retaining the cocking knob 38 in the housing 42. While the middle portion 89 of the cocking knob 38 is engaged with the inwardly extending shoulder 105 of the housing 42, the cocking knob 38 can be rotated with relation to the housing 42 in order to "cock" the lancet device 30 and prepare the lancet device 30 for firing. As shown in FIG. 4*b*, an interior surface of the bottom portion 90 of the cocking knob includes a lug or stop 93 which, as will be described later herein, engages a flange 152 on the cam 122 at the completion of the "firing" operation of the device. The cocking feature as well as the firing feature will be described more fully later hereinbelow.

As shown in FIGS. 2, 17 and 24, formed on an internal surface 108 of the cocking knob 38 is a thread 110 for receiving a thread 112 on a depth adjustment screw 114 within the lancet device 30. The thread 112 on the depth adjustment screw 114 has an abrupt start and an abrupt termination, and runs in a mating female thread 110 on the internal surface 108 of the cocking knob 38 which also has an abrupt thread, but includes a chase stop toward its outer end. The stop prevents the depth adjustment screw 114 from being totally unscrewed of the cocking knob 38. As shown in FIGS. 2, 10*c*, 11*c*, 17 and 24, a bore 216 extends through the depth adjustment screw 114, and (shown in FIGS. 2, 17 and 24) the ejector rod 78 extends through the bore 216. The depth adjustment screw 114 has a top portion 119 and a bottom portion 120. While the thread 112 is formed on the top portion 119 of the depth adjustment screw 114, the bottom portion 120 of the depth adjustment screw 114 snaps into engagement with a cam 122 as shown in FIG. 2, 11*c*, 17 and 24. To facilitate the snapping engagement between the cam 122 and the depth adjustment screw 114, a fork 127 is formed in the bottom portion 120 of the depth adjustment screw 114, and at the end 126 of the fork 127 are two one-way barbs 124 which engage against an inwardly extending shoulder 128 on an internal surface 130 of the cam 122. As shown in FIGS. 10*b*, 10*c* and 11*c*, the bottom portion 120 of the depth adjustment screw 114 includes a slot 132 which defines the fork 127. The slot 132 allows the one-way barbs 124 on the bottom portion 120 to be urged inward toward each other allowing the depth adjustment screw 114 to be snapped into engagement with the cam 122. However, after the ejector rod 78 is inserted into the depth adjustment screw 114, the one-way barbs 124 do not readily collapse or release from the cam 122.

The internal surface 108 of the cocking knob 38 also forms a shoulder 116 for engagement with a straight compression spring 118 which extends between the platform 81 of the ejector rod 78 and the shoulder 116 of the cocking knob within the lancet device 30. As shown in FIGS. 2, 17 and 24, the compression spring 118 surrounds a portion of the top portion 119 of the depth adjustment screw 114 within the lancet device 30.

As shown in FIGS. 2, 17 and 24, the cam 122 has a central bore 134, and a first end 136 of the cam 122 receives the bottom portion 120 of the depth adjustment screw 114. An opposite end 138 of the cam 122 receives a cam engaging portion 140 of a lancet holder 142. The engagement between the cam 122 and the depth adjustment screw 114 is such that the depth adjustment screw 114 and the cam 122 can rotate relative to each other. The engagement between the cam 122 and the lancet holder 142 is such that the lancet holder 142 can slide in relation to the cam 122 within the cam central bore 134, and the cam 122 can rotate relative to the lancet holder 142. As shown in FIG. 8*a*, 8*b*, 8*c*, 8*d*, 9, 10*a*, 10*b*, 11*a* and 11*b*, at the end 138 of the cam 122, on the external surface 144 of the cam 122, is a lip 146. The lip 146 is round with a flattened portion 148 which does not engage against the drive spring 96 but enables the assembling of the spring 96 onto the cam 122. A flange 152 on the external surface 144 of the cam 122 anchors a tang 154 at the end of the drive spring 96. To this end, the flange 152 is provided with an undercut 156 for anchoring the tang 154. A face cam 158 is formed at the other end 138 of the cam 122, and the face cam 158 comprises two opposing crests 160 separated by two opposing valleys 162. As shown in FIGS. 11*a*, 11*b*, 18, 20, 22 and 23, two opposing cam follower members 164 on the lancet holder 142 press against the face cam 158 of the cam 122. As mentioned, and as depicted in FIGS. 3*a* and 3*b*, the cam follower members 164 are engaged in the grooves 63 provided by the U-shaped walls 61 in the halves 52 and 54 of the housing 42. While the drawings depict the lancet holder 142 as having two cam follower members 164, one having ordinary skill in the art should recognize that the lancet holder may be provided with a single cam follower member 164, or with more than two cam follower members 164. Additionally, one having ordinary skill in the art should recognize that it is not imperative that the cam follower members 164 be shaped as is depicted in the drawings.

The overall shape of the lancet holder 142 can be seen in FIGS. 7*a*, 7*b*, 7*c* and 7*d*, and the overall shape of the depth adjustment screw 114, the cam 122, and the lancet holder 142 can be seen in FIGS. 10*a*, 10*b* and 10*c*. The cam 122 has two opposing trigger stops 166 thereon for engaging a sear member 168 on the trigger 44, as shown in FIGS. 18, 20 and 23. Engagement of the cam 122 with the depth adjustment screw 114 and the lancet holder 142 can be seen in FIGS. 11*a*, 11*b* and 11*c*.

Opposite the cam engaging portion 140 of the lancet holder 142 is a lancet holding portion 170. The lancet holding portion 170 of the lancet holder 142 has a T-shaped slot 172 therein for facilitating the frictional securement of a lancet 174 as shown in FIGS. 2, 17 and 24. The "universal" shape of the lancet holding portion 170 of the lancet holder 142 provides that the lancet device 30 may be used with the most popular, present day lancets. A seat portion 176 of the lancet 174 is frictionally held by the lancet holding portion 170 of the lancet holder 142. Opposite the seat portion 176 of the lancet 174 is a lancing needle 178. The lancet holder 142 has a central bore 180 for receiving the ejector rod 78 and the ejector blade 82. As a result, the ejector blade 82 pushes against the lancet 174 when the thumb button 34 is pushed. The lancet holder 142 has a spring engaging ridge 182 for engaging against one end 184 of a tapered, compression return spring 186. The other end 188 of the return spring 186 is engaged against a shoulder 190 within the housing 42. The return spring 186 presses the lancet holder 142 against the cam 122, and particularly presses the cam follower members 164 on the lancet holder 142 against the face cam 158 of the cam 122.

The trigger 44 is illustrated alone in FIG. 5. As mentioned, the trigger 44 includes a sear member 168 for engaging with two trigger stops 166 on the cam 122. The trigger 44 also includes a finger engaging portion 192 which is pressed to fire the lancet device 30. The firing of the lancet device 30 will be described more filly later hereinbelow. The trigger 44 also includes opposing pivot bearing receiving members 194 for receiving pivot bearings 196 within the housing 42. The pivot bearings 196 extend through a hole 198 in each pivot bearing receiving member 194 on the trigger 44, and allow the trigger 44 to pivot about the pivot bearings 196 when the finger engaging portion 192 of the trigger 44 is pressed causing the sear member 168 to disengage from either one of the trigger stops 166 on the cam 122. As shown, the pivot bearings 196 straddle cam 122, but do not physically touch or intersect the cam 122.

As mentioned, the lancet device 30 is intended to be used to pierce a fingertip in order to obtain blood for diagnostic purposes. Operation of the lancet device 30 for such a purpose will now be described in detail. As shown in FIG. 1, the housing 42, the top portion 36 of the cocking knob 38, and the portion of the tip platform 48 which defines part of the external surface 32 of the lancet device 30 are all generally rectangular in cross-section. This provides the lancet device 30 with generally a rectangular-shaped body. This generally rectangular shape provides that the lancet device 30 does not roll in the user's hand and is easy to orient and grip during use. The lancet device 30 is compact and generally designed and shaped to be held much like a writing instrument during use.

First, a lancet 174 is loaded into the lancet holder 142 of the lancet device 30. To load the lancet 174, the seat portion 176 of the lancet 174 is inserted into the end 50 of the housing 42, and is frictionally seated in the lancet holding portion 170 of the lancet holder 142 by pressing the lancet 174 thereinto. When the lancet 174 is pushed into the lancet holding portion 170 of the lancet holder 142, the t-shaped slot 172 provides some give so that the lancet holding portion 170 of the lancet holder 142 can receive the lancet 174. After the lancet 174 is seated in the lancet holder 142 of the lancet device 30, a cap (not shown) is removed from the lancet 174 in order to expose the lancing needle 178. The tip platform 48 is then secured to the housing 42 of the lancet device 30 by applying the tip platform 48 to the end 50 of the housing 42 and turning the tip platform 48 through a ninety degree, or one-quarter turn, rotation as shown in FIG. 14. This rotation causes the flanges 64 on the tip platform 48 to ride in the helical grooves 62 and 74 near the end 50 of the housing 42. In this manner, the installation of the tip platform 48 is a quarter-turn bayonet-type installation. FIG. 14 shows the flanges 64 when the flanges 64 first interact with the helical grooves 62 and 74. FIG. 15 shows the flanges 64 in the helical grooves 62 and 74 after the tip platform 48 has been fully screwed into the end 50 of the housing 42, and FIG. 16 shows the flanges 64 engaged with the helical grooves 62 and 74 after the tip platform 48 has been fully screwed into the end 50 of the housing 42. When the tip platform 48 is screwed into the end 50 in the housing, a hole 200 on the tip platform 48 is aligned with the lancing needle 178 such that the lancing needle 178 can extend through the hole 200 in the tip platform 48 when the lancet device 30 is fired as shown in FIG. 22, or when the lancing needle 178 is being ejected from the lancet device 30, as shown in FIG. 24.

After the lancet 174 is seated in the lancet holder 142, and after the tip platform 48 has been screwed into the end 50 of the housing 42, the thumb button 34 is turned to set the extent at which the lancing needle 178 will extend through the opening 200 in the tip platform 48 when the lancet device 30 is fired. Setting the extent at which the lancing needle 178 will extend though the hole 200 in the tip platform 48 essentially controls the depth at which the lancing needle 178 will lance the skin of the fingertip when the lancet device 30 is fired. Being able to adjust the depth at which the lancing needle 178 will lance the skin is important because different people benefit most from different depths of piercing. For example, an eighty year old woman may require less piercing depth than a fourteen year old boy. Therefore, being able to adjust the depth at which the lancing needle 178 of the lancet device 30 will lance the skin is a desirable feature of the lancet device 30. This is especially true in a clinical setting where a nurse will use the lancet device 30 on many different patients having different lancing depth requirements. To facilitate the setting of the lancing depth of the lancet device 30, indicia may be provided on the thumb button 34 to indicate the lancing depth at which the lancet device 30 is set.

Adjustment of the lancing depth will now be described. When the thumb button 34 is turned as shown in FIG. 17, the ejector rod 78 rotates therewith. When the ejector rod 78 rotates, the depth adjustment screw 114 also rotates because of radial engagement between the ejector rod 78 and the depth adjustment screw 114. There is no axial coupling in order to allow unimpeded axial operation of the ejector assembly. The threaded engagement of the thread 112 on the depth adjustment screw 114 with the thread 110 on the cocking knob 38 provides that the depth adjustment screw 114 moves axially relative to both the cocking knob 38 and the housing 42 when the thumb button 34 is turned. Because the cam 122 is snapped into engagement with the depth adjustment screw 114 and the lancet holder 142 is pressed into engagement with the face cam 158 of the cam 122 by the return spring 186 and the cam follower members 164 slide in the grooves 63 provided by the U-shaped walls 61 on the interior surface of the housing 42, the cam 122 and lancet holder 142 also move axially within the lancet device 30 when the thumb button 34 is turned. The threaded engagement between the depth adjustment screw 114 and the cocking knob 38 provides that the lancet holder 142 moves axially toward the end 50 of the housing 42 and away from the thumb button 34 when the thumb button 34 is rotated clockwise relative to the cocking knob 38. However, the cam 122 does not rotate along with the depth adjustment screw 114 when the thumb button 34 is turned because, at this time, the sear member 168 of the trigger 44 is engaged against one of the trigger stops 166 on the cam 122. Additionally, the U-shaped walls 61 prevent the lancet holder 142 from rotating. As a result of having rotated the thumb button 34 clockwise, the lancing needle 178 starts out closer to the hole 200 in the tip platform 48 before the lancet device 30 is fired. Therefore, the lancing needle 178 will more fully extend through the hole 200 in the tip platform 48 when the lancet device 30 is fired, and there will be more piercing depth by the lancing needle 178. Likewise, the threaded engagement between the depth adjustment screw 114 and the cocking knob 38 provides that the cam 122, lancet holder 142 and lancet 174 move axially away from the tip platform 48 when the thumb button 34 is rotated in a counter-clockwise direction relative to the housing 42. Therefore, the lancing needle 178 starts out further away from the hole 200 in the tip platform 48 before the lancet device 30 is fired, and less of the lancing needle 178 will extend through the hole 200 in the tip platform 48 when the lancet device 30 is fired so there will be less piercing depth by the lancing needle 178.

After the lancet 174 and tip platform 48 are in place on the lancet device 30, and the piercing depth is set, the lancet device 30 can be prepared for firing, or "cocked." To cock the lancet device 30, one securely holds the housing 42 while turning the cocking knob 38 through a rotation of one hundred eighty degrees in a clockwise direction relative to the housing 42. This rotation of the cocking knob 38 is shown in FIG. 18. As the cocking knob 38 is rotated relative to the housing 42, the end 94 of the drive spring 96 within the lancet device 30 also rotates because of being engaged with the slot 92 in the cocking knob 38. The cam 122 does not rotate most of the time the cocking knob 38 is rotated because the sear member 168 of the trigger 44 engages against a trigger stop 166 on the cam 122 after the first couple of degrees of rotating the cocking knob 38. While rotating the cocking knob 38, the stop 93 moves out of contact with the flange 152 on the cam 122. Because the cam 122 is restrained from rotating while the lancet device 30 is being cocked, the lancing needle 178 does not extend from the hole 200 in the tip platform 48 during cocking. As a result, the risk of being accidentally stuck by the lancing needle 178 while cocking the lancet device 30 is minimized. Also, because the cam 122 does not rotate when the cocking knob 38 is rotated, the tang 154 on the end of the drive spring 96 does not move, and is held in place by the flange 152 on the cam 122. As a result, when the cocking knob 38 is rotated, the drive spring 96 loads within the lancet device 30, between the cocking knob 38 and the cam 122. As the cocking knob 38 is rotated, the one way detent finger 70 on the cocking knob 38 moves towards one of the stops 68 or 76 on the internal surface of the housing 42 of the lancet device 30. Shown in FIG. 18 is the one way detent finger 70 moving towards stop 68 as the cocking knob 38 is rotated. This movement is also shown in FIG. 19. As the one way detent finger 70 on the cocking knob 38 initially meets one of the stops 68 on the housing 42 as the cocking knob is rotated, the flexible finger 98 moves axially inward allowing the detent flange 100 thereon to clear and move past the stop 68 on the housing 42. The angled wall 102 of the detent flange 100 further provides that the detent flange 100 can clear the stop 68 without requiring an excessive amount of rotational force to be applied to the cocking knob 38. Once the detent flange 100 on the cocking knob 38 clears and moves past the stop 68 on the housing 42, the cocking knob 38 is restricted from rotating in the opposite direction. After the cocking knob 38 is rotated enough to cause the detent flange 100 on the cocking knob 38 to clear the stop 68 on the housing 42, the drive spring 96 is fully loaded between the cocking knob 38 and the cam 122. After the cocking knob 38 has been fully rotated, the loaded drive spring 96 cannot unload causing the cocking knob 38 to rotate because the detent flange 100 on the cocking knob 38 is secured against the stop 68 on the housing 42 as shown in FIGS. 20 and 21. Also, the loaded drive spring 96 cannot unload causing the cam 122 to rotate because of the sear member 168 of the trigger 44 being engaged against one of the trigger stops 166 on the cam 122.

After the cocking knob 38 has been fully rotated one hundred eighty degrees relative to the housing 42 causing the detent flange 100 on the cocking knob 38 to clear the stop 68 on the housing, the lancet device 30 is "cocked", in other words, is properly prepared for operation, or "firing."

Firing of the lancet device will now be described. Before firing the lancet device 30, the tip platform 48 is applied against the fingertip which is to be pierced or lanced by the lancet device 30. After the tip platform 48 is applied against the fingertip, the lancet device can be fired. To fire the lancet device, the finger engaging portion 192 of the trigger 44 is pressed. When the trigger 44 is pressed, the sear member 168 of the trigger 44 withdraws and disengages from one of the trigger stops 166 on the cam 122 as shown in FIG. 22. When the sear member 168 withdraws from the trigger stop 166, the cam 122 is no longer restricted from rotating. As a result, the drive spring 96 which became loaded between the cocking knob 38 and the cam 122 can unload into the cam 122 causing the cam 122 to rotate. As the cam 122 rotates, the cam follower members 164 press on the face cam 158 of the cam 122. The cam follower members 164 on the lancet holder 142 are kept in contact with the face cam 158 of the cam 122 while the cam 122 rotates because of compression of the lancet holder return spring 186 between the ridge 182 on the lancet holder 142 and the shoulder 190 in the housing 42. Therefore, as the cam 122 rotates, the cam follower members 164 ride along the face cam 158 of the cam 122, and more particularly ride along the valleys 162, up to the crests 160, and back into the valleys 162 when the lancet device 30 is fired. Additionally, the cam follower members 164 ride within the grooves 63 provided by the U-shaped walls 61 on the interior surface of the housing (see FIGS. 3a and 3b). The U-shaped walls 61 prevent the lancet holder 142 from rotating with the cam 122, and act to stabilize axial movement of the lancet holder 142. Further, the front of the U-shaped walls 61 act as a stop for preventing over extension of the lancet holder 142. This riding of the cam follower members 164 is shown in the progression from FIG. 20 to FIG. 22 to FIG. 23. FIG. 20 shows the lancet device 30 immediately before firing. At this time, the cam follower members 164 are held against the valleys 162 of the cam face 158 of the cam 122. As a result, the lancing needle 178 is not extended out the hole 200 in the tip platform 48. FIG. 22 shows the lancet device 30 while the lancet device 30 is firing. At this time, the cam 122 is in the middle of rotating and the cam follower members 164 have ridden up the valleys 162 of the face cam 158 and up to the crests 160. As a result, the lancing needle 178 extends out the hole 200 in the tip platform 48 and can lance a fingertip. As shown in FIG. 21, while the cam 122 is rotating, the detent flange 100 is kept forced up against the stop 68 in the housing. FIG. 23 shows the lancet device 30 immediately after firing. At this time, the cam follower members 164 have ridden from the crests 160 back into the valleys 162 of the cam face 158 of the cam 122. As a result, the lancing needle 178 has retracted back into the hole 200 in the tip platform 48.

While the lancet device 30 is firing, the cam 122 rotates almost one hundred eighty degrees. The flange 152 on the cam 122 impacts the mating stop 93 on the interior surface of the cocking knob 38 (see FIG. 4b) and arrests the rotation of the cam 122 a few degrees before the next, opposing trigger stop 166 reaches the sear member 168 on the trigger 44, at which time the lancet device 30 is ready to be cocked again causing the stop 93 on the cocking knob 38 to rotate away from the flange 152 against which the stop 93 had contacted to stop over rotation of the cam 122. After the lancet device 30 has completely fired, the detent flange 100 on the cocking knob 38 is still secured against the stop 68 on the housing 42. However, the lancet device 30 can be cocked again by rotating the cocking knob 38 causing the detent flange 100 on the cocking knob 38 to move toward and clear the other, opposing stop 76 on the housing 42 in much the same manner as was described above with relation to movement of the detent flange 100 past the stop 68.

Therefore, the cocking knob 38 is rotated one hundred eighty degrees clockwise while the cam 122 remains still during cocking of the lancet device 30, and the cam 122 rotates one hundred eighty degrees clockwise while the cocking knob 38 remains still during firing of the lancet device 30. In this manner, the cam 122 follows the cocking knob 38 in half-turns through repeated cocking and firing of the lancet device 30. As a result, the lancet device 30 structured in accordance with the present invention obviates the need for any type of cocking knob return spring because the cocking knob 38 does not return to a home position after firing the lancet device 30.

After the lancet device 30 has been fired, the lancet 174 must be replaced before the lancet device 30 is used again. The lancet device 30 in accordance with the present invention provides that the lancet 174 can be easily ejected from the lancet device 30 along with the tip platform 48 without having to physically touch either the tip platform 48 or the lancet 174. This feature is especially beneficial in a clinical setting where a nurse is using the lancet device 30 on several different patients.

The functioning of the lancet device 30 to simultaneously eject the lancet 174 and the tip platform 48 will now be described. To eject the lancet 174 from the lancet device 30, one pushes the thumb button 34 into the opening 88 in the cocking knob 38 as shown in FIGS. 24 and 25. As a result of pressing the thumb button 34, the ejector rod 78 and the ejector blade 82 move axially within the lancet device 30 toward the tip platform 48, and the ejector blade 82 pushes on the seat portion 176 of the lancet 174, thus urging the lancet 174 out of engagement with the lancet holding portion 170 of the lancet holder 142. The return spring 186 must be of sufficient strength to resist compression while the lancet 174 is being pushed out of engagement with the lancet holder 142. When the thumb button 34 is pushed into the opening 88 in the cocking knob 38, the compression spring 118 compresses between the shoulder 116 on the internal surface 108 of the cocking knob 38 and the platform 81 of the ejector rod 78 within the lancet device 30. As the thumb button 34 is further pushed, the compression spring 118 is further compressed, and the lancet 174 gets further pushed by the ejector blade 82 until the lancing needle 178 of the lancet 174 extends out of the hole 200 in the tip platform 48 at which time the lancet 174 contacts and pushes the tip platform 48. This is shown in FIG. 24. This pushing on the tip platform 48 by the lancet 174 causes the flanges 64 on the tip platform. 48 to move inward, toward the central axis 67 of the tip platform 48, and clear the helical grooves 62 and 74 on the housing 42, as shown in FIG. 26. Once the flanges 64 on the tip platform 48 clear the helical grooves 62 and 74, any further pushing on the thumb button 34 causes the tip platform 48 to fall away from the housing 42 and therefore from the lancet device 30 in general. At about the time when the flanges 64 on the tip platform 48 clear the helical grooves 62 and 74, the seat portion 176 of the lancet 174 disengages from the lancet holder 142. Therefore, at about the time the tip platform 48 falls away from the housing 42, so does the lancet 174. When the thumb button 34 is released, the compression spring 118 pushes the thumb button 34 out from the opening 88 in the cocking knob 38, back to its original position. In this manner, the lancet device 30 provides for the touchless, simultaneous ejection of both the lancet 174 and the tip platform 48. However, one having ordinary skill in the art would recognize that it is possible to first manually unscrew the tip platform 48 before ejecting only the lancet 174 by pressing the thumb button 34, and that this may, in fact, be desirable in some settings such as where the lancet device 30 is being personally used at home and, therefore, it is desirable to retain the tip platform 48 for re-use. Regardless, by providing that the thumb button 34 is at the end of the lancet device 30 rather than at some other location on the lancet device 30, the possibility that the thumb button 34 will be accidentally pushed and the lancet 174 inadvertently ejected is minimized because the location of the thumb button 34 on the lancet device 30 provides that it is easy to avoid mistakenly pressing the thumb button 34 while cocking or firing the lancet device 30.

As described above, the lancet device 30 in accordance with the present invention provides many advantages over the prior art. For example, by providing that the lancet device 30 is held like a writing instrument and that the trigger 44 on the lancet device 30 is relatively close to the firing end the lancet device 30 is easy to orient and grip during use. Also, the lancet device 30 is compact and has a generally rectangular overall cross-sectional body shape, thus preventing rolling during use and further providing that the lancet device 30 is easy to grip. Furthermore, the lancet device 30 can be easily cocked merely by rotating the cocking knob 38 one hundred eighty degrees without having to apply an excessive amount of rotational force. Additionally, the lancet device 30 minimizes parts by providing that the thumb button 34 doubles as both a depth adjustment knob when turned, and an ejector button when pushed. Still further, the lancet device 30 in accordance with the present invention provides that the lancing needle 178 does not extend or become exposed while the lancet device 30 is cocked. This feature is important in order to prevent accidental sticking by the lancing needle 178. Finally, the lancet device 30 requires minimal forces from the user in order to fire the lancet device 30, and simultaneously eject both the lancing needle 178 and tip platform 48 from the lancet device 30 after firing. Still other advantages of the lancet device 30 structured in accordance with the present invention would be readily apparent to one having ordinary skill in the art.

While a preferred embodiment of the present invention is shown and described, it is envisioned that those skilled in the art may devise various modifications and equivalents without departing from the spirit and scope of the invention. The invention is not intended to be limited by the foregoing disclosure.

What is claimed is:

1. A lancet device for lancing skin with a lancing needle of a lancet, said lancet device comprising: a housing; a lancet holder-within said housing engageable with said lancet and moveable along a longitudinal axis of said housing; a cam having an end surface engageable with said lancet holder; cocking structure; biasing means between said cocking structure and said cam; and a trigger engageable with said cam for preventing the rotation of said cam during actuation of said cocking structure, said actuation of said cocking structure causing said biasing means to become loaded between said cam and said cocking structure wherein upon disengagement of said trigger from said cam, said cam rotates, said rotation of said cam causing said lancet holder to move generally along said longitudinal axis of said housing.

2. The lancet device as recited in claim 1, further comprising structure generally preventing said lancet holder from moving generally along said longitudinal axis of said housing during actuation of said cocking structure.

3. The lancet device as recited in claim 2, wherein said structure generally preventing said lancet holder from moving comprises a biasing member urging said lancet holder against said cam.

4. The lancet device as recited in claim 3, wherein said biasing member comprises a spring.

5. The lancet device as recited in claim 1, said lancet holder including at least one cam follower member, said end surface of said cam including alternating crests and valleys along which said cam follower member rides upon rotation of said cam thereby causing said lancet holder to move generally along said longitudinal axis of said housing.

6. The lancet device as recited in claim 5, wherein said cam follower member is engaged with structure on an interior surface of said housing thereby generally preventing said lancet device from rotating relative to said housing upon rotation of said cam.

7. The lancet device as recited in claim 1, said biasing means comprising a spring which is generally carried on said cam, said spring having a first end engaged with said cam and having a second end engaged with said cocking structure.

8. The lancet device as recited in claim 1, said cocking structure comprising a cocking knob which engages the interior surface of said housing thereby generally locking said cocking knob in place relative to said housing after said cocking knob has been rotated causing said biasing means to load between said cocking knob and said cam.

9. The lancet device as recited in claim 1, said cocking structure comprising a cocking knob having a bore therein which receives a button which is configured to selectively effect disengagement of said lancet from said lancet holder and effect adjustment of a lancing depth of the lancing needle.

10. The lancet device as recited in claim 1, further comprising an assembly operatively coupled to said lancet holder, said assembly rotatable and axially moveable within said housing, said assembly having a first end engageable with said lancet when said lancet is engaged with said lancet holder, said assembly having a second end external to said housing, said assembly being configured such that turning said second end of said assembly causes said assembly to rotate within said housing thereby causing said lancet holder to move axially within said housing, said axial movement of said lancet holder in said housing adjusting a lancing depth of said lancing needle, and said assembly being configured such that pressing said second end of said assembly toward said housing causes said assembly to move axially within said housing and engage against said lancet thereby causing said lancet to disengage from said lancet holder.

11. The lancet device as recited in claim 10, further comprising an endpiece having an aperture formed thereon for receiving said lancing needle, wherein said housing has an end configured for engagement with said endpiece, said assembly being configured such that pressing said second end of said assembly toward said housing causes said assembly to move axially within said housing and engage against said lancet thereby causing said lancet to urge from said lancet holder and contact said endpiece when said endpiece is engaged with said end of said housing, said engagement between said endpiece and said end of said housing being such that said contact between lancet and said endpiece causes said endpiece to disengage from said end of said housing.

12. The lancet device as recited in claim 10, wherein said assembly is threadably engaged with said cocking structure, said threadable engagement providing that turning said second end of said assembly causes said assembly to rotate within said housing thereby causing said lancet holder to move axially within said housing.

13. The lancet device as recited in claim 12, wherein said assembly comprises a depth adjustment screw having a bore; and an ejector rod extending through said bore in said depth adjustment screw, wherein said depth adjustment screw is threadably engaged with said cocking structure, and wherein said ejector rod and said depth adjustment screw are engaged with each other such that rotating said ejector rod causes said depth adjustment screw to rotate but said ejector rod can move axially within said bore relative to said depth adjustment screw when said second end of said assembly is pressed toward said housing.

14. The lancet device as recited in claim 11, wherein said endpiece includes structure which moves radially inward upon said endpiece being contacted by said lancet thereby providing that said endpiece disengages from said end of said housing.

15. The lancet device as recited in claim 14, said endpiece including flanges and helical slots, said end of said housing including grooves for receiving said flanges on said endpiece, wherein said helical slots of said endpiece allow said flanges of said endpiece to move radially inward and disengage from said grooves on said end of said housing upon said endpiece being contacted by said lancet.

16. The lancet device as recited in claim 10, further comprising an endpiece having an aperture formed thereon for receiving said lancing needle, wherein said housing has an end configured for engagement with said endpiece, and wherein said trigger is closer to said aperture of said endpiece when said endpiece is engaged with said end of said housing than to said second end of said assembly.

17. The lancet device as recited in claim 10, further comprising an endpiece having an aperture formed thereon for receiving said lancing needle, wherein said housing has an end configured for engagement with said endpiece, said second end of said assembly being opposite said aperture formed in said endpiece for receiving said lancing needle.

18. The lancet device as recited in claim 1, further comprising an endpiece having an aperture formed thereon for receiving said lancing needle, wherein said housing has an end configured for engagement with said endpiece, a nd wherein said endpiece becomes filly engaged with said housing by rotating said endpiece relative to said end of said housing through a generally ninety-degree rotation.

19. The lancet device as recited in claim 1, said cocking structure including a cocking knob received by said housing, wherein said biasing means is loaded by rotating said cocking knob through a generally one-hundred eighty degree rotation.

20. A lancet device for lancing skin with a lancing needle of a lancet, said lancet device comprising: a housing; a lancet holder within said housing engageable with said lancet and moveable along a longitudinal axis of said housing, said lancet holder including at least one cam follower member; a cam having an end surface; biasing means engaged with said housing and said lancet holder, said biasing means pressing said cam follower member into engagement with said end surface of said cam, said end surface of said cam including alternating crests and valleys along which said cam follower member rides upon rotation of said cam thereby causing said lancet holder to move generally along said longitudinal axis of said housing.

21. The lancet device as recited in claim 20, further comprising cocking structure; a spring engaged between said cocking structure and said cam; and a trigger engageable with said cam for preventing the rotation of said cam during actuation of said cocking structure and preventing movement of said lancet holder along a longitudinal axis of said housing, said actuation of said cocking structure causing said spring to become loaded between said cam and said cocking structure wherein said cam rotates upon disengagement of said trigger from said cam, said rotation of said cam causing said cam follower member to ride along said end surface of said cam, thereby causing said lancet holder to move generally along the longitudinal axis of said housing.

22. The lancet device as recited in claim 20, wherein said cam follower member is engaged with structure on an interior-surface of said housing thereby generally preventing said lancet device from rotating relative to said housing upon rotation of said cam.

* * * * *

UNITED STATES PATENT AND TRADEMARK OFFICE
CERTIFICATE OF CORRECTION

PATENT NO. : 6,156,050
DATED : December 5, 2000
INVENTOR(S) : Richard M. Davis and Rowland W. Kanner It is certified that error appears in the above-identified patent and that said Letters Patent is hereby corrected as shown below:

<u>Column 16,</u>
Lines 12-13, "a nd wherein said endpiece becomes filly" should read -- and where in said endpiece becomes fully --.

Signed and Sealed this

Sixth Day of November, 2001

Attest:

*Nicholas P. Godici*

NICHOLAS P. GODICI
*Attesting Officer    Acting Director of the United States Patent and Trademark Office*